US 6,194,391 B1

(12) United States Patent
Schinazi et al.

(10) Patent No.: US 6,194,391 B1
(45) Date of Patent: Feb. 27, 2001

(54) 3'-AZIDO-2',3'-DIDEOXYURIDINE ADMINISTRATION TO TREAT HIV AND RELATED TEST PROTOCOL

(75) Inventors: Raymond F. Schinazi, Decatur, GA (US); Martin L. Bryant; Maureen W. Myers, both of Carlisle, MA (US)

(73) Assignees: Emory University, Atlant, GA (US); Norvirio Pharmaceuticals Limited, Grand Cayman (KY)

( * ) Notice: Subject to any disclaimer, the term of this patent is extended or adjusted under 35 U.S.C. 154(b) by 0 days.

(21) Appl. No.: 09/339,133

(22) Filed: Jun. 24, 1999

Related U.S. Application Data

(60) Provisional application No. 60/090,552, filed on Jun. 24, 1998, and provisional application No. 60/132,126, filed on Apr. 30, 1999.

(51) Int. Cl.[7] .............................. A61K 31/70; C12Q 1/68
(52) U.S. Cl. .................. 514/50; 514/45; 514/46; 514/47; 514/48; 514/49; 514/51; 514/252; 514/262; 435/6
(58) Field of Search .................. 435/6; 514/45, 514/46, 47, 48, 49, 50, 51, 252, 262

(56) References Cited

U.S. PATENT DOCUMENTS

| | | | |
|---|---|---|---|
| 4,916,122 | 4/1990 | Chu et al. ........................ 514/50 |
| 5,099,010 | 3/1992 | Lin et al. ....................... 536/28.2 |
| 5,103,002 | 4/1992 | Wieland . | |
| 5,110,987 | 5/1992 | Liotta et al. . | |
| 5,190,876 | 3/1993 | Merrill et al. . | |
| 5,232,837 | 8/1993 | Merrill et al. . | |
| 5,234,913 | * 8/1993 | Furman et al. ................. 514/49 |
| 5,409,810 | 4/1995 | Larder et al. ................... 435/5 |
| 5,413,999 | * 5/1995 | Vacca et al. ................ 514/231.5 |
| 5,430,169 | 7/1995 | Boumendjel et al. . | |
| 5,459,057 | 10/1995 | Merrill et al. . | |
| 5,463,092 | 10/1995 | Kumar et al. . | |
| 5,488,166 | 1/1996 | Hudlicky . | |
| 5,518,879 | 5/1996 | Merrill et al. . | |
| 5,521,161 | * 5/1996 | Malley et al. ................. 514/45 |
| 5,545,620 | * 8/1996 | Wahl et al. .................... 514/12 |
| 5,599,914 | 2/1997 | Wiegand et al. . | |
| 5,604,209 | * 2/1997 | Ubasawa et al. ................ 514/45 |
| 5,610,040 | 3/1997 | Smeets et al. . | |
| 5,616,578 | * 4/1997 | Otto ............................... 514/218 |
| 5,627,186 | * 5/1997 | Cameron et al. ............... 514/274 |
| 5,635,536 | 6/1997 | Lyons . | |
| 5,637,589 | * 6/1997 | Lee et al. ....................... 514/291 |
| 5,650,412 | * 7/1997 | Kim et al. ...................... 514/253 |
| 5,668,132 | * 9/1997 | Vacca et al. ................... 514/252 |
| 5,670,520 | * 9/1997 | Gelfand et al. ................. 514/314 |

(List continued on next page.)

FOREIGN PATENT DOCUMENTS

| | | |
|---|---|---|
| 0 217 580 | 4/1987 | (EP) . |
| 0 821 068 | 1/1998 | (EP) . |
| 2181128 | 4/1987 | (GB) . |
| WO 97 10817 | 3/1997 | (WO) . |
| WO 97 26891 | 7/1997 | (WO) . |

OTHER PUBLICATIONS

Bennun et al., *Infect. & Immun.*, 57:969–74, 1989. (Issue No. 3, Mar., 1989).
Bell, R., et al. *Cold Spr. Harbor Sym. Quant. Biol.* 53:103, 1988.
Buehrer and Bell, *J. Biol. Chem.* 267:3154–3159, 1992.(Iss. No. 5; Feb. 15, 1992).
Buehrer and Bell, *Adv. Lipid Res.* 6:59–67, 1993.
Crossman and Hirschberg, *J. Biol. Chem*, 252:5815–5819, 1977. (Iss. #16; Aug. 25, 1977).
Farkas–Himsley et al., *Proc. Natl. Acad. Sci.* (USA) 92:6996–7000, 1995.(#15; Jul. 18, 1995).
Hakomori,, *J. Biol. Chem.* 265:18713–18716, 1990. (Iss. No. 31; Nov. 5, 1990).
Hannun et al., *J. Bio. Chem.* 261:12604–12609, 1986. (Iss. No. 27; Sep. 25, 1986).
Hannun, J. Biol. Chem. 269:3125–3128, 1994. (Iss. No. 15; Feb. 4, 1994).
Hannun and Obeid, *Trends Biochem, Sci.* 20:73–77, 1995. (Feb. 1995).
Jacewicz et al., *J. Clin. Invest.* 96:1328–1335, 1995. (Sep. 1995).
Jefferson, A. and Schulman, H., *J. Biol. Chem.* 263:15241, 1988. (#30; Oct. 25, 1988).
Karlsson, K. A., *Chem. Phys. Lipids*, 5:6–43, 1970. (Iss. No. 1; Oct., 1970).
Kawai, G. et al., "Stimulatory effect of certain plant sphingolipids on fruiting of Schizophyllum commune," *J. of Biol. Chem.*, 261(2), 1986 779–784. (Jan. 15, 1986).
Keusch et al., *Infect. & Immun.* 63: 1138–1141; 1995. (Iss. No. 3; Mar., 1995).
Kolesnick, *Cell* 77:325–328, 1994. (Iss. No. 3; Mar. 6, 1994).

(List continued on next page.)

*Primary Examiner*—Paul J. Killos
*Assistant Examiner*—L. E. Crane
(74) *Attorney, Agent, or Firm*—Sherry M. Knowles; King & Spalding

(57) ABSTRACT

It has been discovered that 3'-azido-2',3'-dideoxyuridine (CS-87) induces a transient mutation in HIV-1 at the 70th codon (K to R, i.e., lysine to arginine) of the reverse transcriptase region of the virus. Based on this discovery, a method and composition for treating HIV is provided that includes administering CS-87 or its pharmaceutically acceptable salt or prodrug to a human in need of therapy in combination or alternation with a drug that induces a mutation in HIV-1 at a location other than the 70th codon of the reverse transcriptase region. This invention can be practiced by referring to the published mutation patterns for known anti-HIV drugs, or by determining the mutation pattern for a new drug.

32 Claims, 9 Drawing Sheets

U.S. PATENT DOCUMENTS

| | | | | |
|---|---|---|---|---|
| 5,700,461 | * | 12/1997 | Schwartz et al. | 424/85.2 |
| 5,703,058 | * | 12/1997 | Schinazi et al. | 514/45 |
| 5,705,522 | * | 1/1998 | Hamedi-Sangsari et al. | 514/423 |
| 5,726,204 | * | 3/1998 | Lee et al. | 514/455 |
| 5,811,390 | * | 9/1998 | Bourinbairar | 514/8 |
| 5,847,165 | * | 12/1998 | Lee et al. | 549/280 |
| 5,849,793 | * | 12/1998 | Pan et al. | 514/546 |
| 5,859,021 | * | 1/1999 | Cameron et al. | 514/274 |
| 5,905,070 | * | 5/1999 | Schinazi et al. | 514/49 |
| 5,910,425 | | 6/1999 | De Boer et al. . | |
| 5,916,911 | | 6/1999 | Shayman et al. . | |

OTHER PUBLICATIONS

Merrill and Wang, *Methods Enzymol,.* 209:427–437, 1992.

Merrill et al., *J. Biol. Chem.* 261:3764–3769, 1986. (Iss. No. 8; Mar. 15, 1986).

Merrill & Sweeley, "Sphingolipids: metabolism and cell signalling," *New Comprehensive Biochemistry: Biochemistry of Lipids, Lipoproteins, and Membranes,* (Vance, D.E. & Vance, J.E., eds.), pp. 309–339, Elsevier Science, Amsterdam, 1996.

Minn, A. J., et al., *Blood* 86: 1903–1910, 1995. (Iss. No. 5; Sep. 1, 1995).

Minn, A. J., et al., *Nature,* 385: 353–357, 1997. (Jan. 23, 1997).

Morrison, Biochim. Biophys. Acta., 176:537–546, 1969.

Muchmore, S. W., et al., *Nature,* 381: 335–341, 1996 (May 23, 1996).

Nilsson, A., *Biochim. Biophy. Acta.* 164:575–584, 1968.

Patent Abstracts of Japan, vol. 095, No. 002, Mar. 31, 1995.

Pittet, D., et al.,*J. Biol. Chem.* 262:10072, 1987 (Iss. No. 21; Jul. 25, 1987).

Robson et al., *J. Lipid. Res.* 35:2060–2068, 1994.(Iss. No. 11; Nov., 1994).

Schmelz et al., *Journal of Nutrition.* 124; 702–712.

Thompson, et al., *Biochem. Pharmacol.* 56: 591–597, 1998.(Iss. No. 4; Aug. 15, 1998.).

Wells, G. B. and Lester, R.L., *J. Biol. Chem.,* 258:10200–10203, 1983(#17; Sep. 10, 1983).

Wilson et al., *J. Biol. Chem.* 261:12616–12623, 1986. (Iss. No. 27; Sep. 25, 1986).

Winicov, I. and Gershengorn, M.,*J. Biol. Chem.* 263:12179, 1988. (#25; Sep. 5, 1988).

Wu et al., *J. Biol. Chem.* 268:13830–13837, 1993.(Iss. No. 19; Jul. 5, 1993).

Merrill, Jr., et al.(I), "Lipids and Lipid–Like Compounds of Fusarium, " Ch. 9 in *Lipids of Pathogenic Fungi,* Prasad et al. (eds.), CRC Press, Inc., New York, NY, 1996, only pp. 199–217 supplied.*

Merrill, Jr., et al.,(II), "Toxicity of Fumonisin $B_1$ for Renal Cell Carcinoma and Other Tumor Lines: A New Class of Possible Chemotherapeutic Agents," Abstract No. 1367 published in *Proceedings American Urological Association.* 155(5), p. 653A (Supplement, May, 1996).*

Vila et al., "Absence of Viral Rebound After Treatment of HIV–Infected Patients with Didanosine and Hydroxycarbamide," *Lancet, 350,* 635–636 (Aug. 30, 1997.*

Colla, et al., *Eur. J. Med. Chem.–Chim. Ther.* 295–301 (1985). (vol. 20, No. 4).

Guatelli et al. *Proc. Natl. Acad. Sci,* (USA), 1874–1878, (Mar. 1990).(vol. 87, No. 5).

Hirsch et al. "Antiretrovral Drug Resistance Testing in Adults with HIV Infection." *JAMA* ; 1998: 1984–1991. (vol. 279, No. 24; Jun. 24, 1998).

Larder et al., *Science,* 243:1731–1734 (1989). (Mar. 31, 1998).

Larder et al., *Science,* 246, 1155–1158 (1989). (Dec. 1, 1989).

Lin and Mancini, *J. Med. Chem.* 26, 544–548 (No. 4; Apr. 1983).

Lin et al., *J. Med. Chem.* 26, 1691–1696 (1983) (Issue No. 12).

Rooke et al. *Antimicrobal Agents Chem,* 988–91 (May 1991). (vol. 35, No. 5).

Schinazi R et al., "Activity of 3'–azido–3'–deoxythymidine nucleotide dimers in primary lymhocytes infected with human immunodeficiency virus type 1." *Antimicrob Agents Chemother* 1990;34:1061–1067. (Issue No. 6, Jun., 1990).

Schinazi RF et al., "Selective inhibition of human immunodeficiency viruses by racemates and enantiomers of cis–5–fluro–1–[2–(hydroxymethyl)–1,3–oxathiolan–5–yl] cytosine." *Antimicrobial Agents Chemother* Nov., 1992;36(11):2423–2431.

Schinazi RF et al., "Characterization of human immunodeficiency virus resistant to oxathiolane–cytosine nucleosides." *International Medical Press* (vol. 4, No. 6, pp. 95–107) Apr., 1993.

Schinazi et al., "Mutations in retroviral genes associated with drug resistance," *International Antiviral News, International Medical Press* 1997. (vol. 4, No. 6, pp. 95–107).

Stuyer L., et al. "Line probe assay for rapid detection of drug–selected mutations in the human immunodeficiency virus type 1 reverse transcriptase gene." *Antimicrob Agents Chemother* 1997:41(2):28491. (Feb., 1997).

* cited by examiner

US 6,194,391 B1

3'-AZIDO-2',3'-DIDEOXYURIDINE ADMINISTRATION TO TREAT HIV AND RELATED TEST PROTOCOL

This application claims priority to U.S. provisional applications, 60/090,552, filed on Jun. 24, 1998, and 60/132,126, filed on Apr. 30, 1999.

In 1983, the etiological cause of AIDS was determined to be the human immunodeficiency virus (HIV). In 1985, it was reported that the synthetic nucleoside 3'-azido-3'-deoxythymidine (AZT) inhibits the replication of human immunodeficiency virus. Since then, a number of other synthetic nucleosides, including 2',3'-dideoxyinosine (DDI), 2',3'-dideoxycytidine (DDC), and 2',3'-dideoxy-2',3'-didehydrothymidine (D4T), have been proven to be effective against HIV. After cellular phosphorylation to the 5'-triphosphate by cellular kinases, these synthetic nucleosides are incorporated into a growing strand of viral DNA, causing chain termination due to the absence of the 3'-hydroxyl group. They can also 2inhibit the viral enzyme reverse transcriptase.

3'-Azido-2',3'-dideoxyuridine (CS-87) is a known compound. It was originally disclosed as an intermediate in the synthesis of an anti-cancer agent. See, for example, U.S. Pat. No. 5,099,010; Lin et al., *J. Med. Chem.* 26, 1691–1696 (1983); Lin and Mancini, *J. Med. Chem.* 26, 544–548; and Colla, et al., *Eur. J. Med. Chem.-Chim. Ther.* 295–301 (1985). Later, it was discovered that the compound has significant anti-HIV activity with lower toxicity than AZT. See U.S. Pat. No. 4,916,122 to Chu and Schinazi. The compound was also included in a broad disclosure of 3'-azido-2',3'-dideoxynucleosides for the treatment of HIV filed by The Wellcome Foundation Limited (see EPA 0 217 580 A2 (Example 64, published Apr. 8, 1987)) and UK Patent Application No. 8622194 (Example 64, published on Apr. 15, 1987). The Wellcome Foundation application included within its broad disclosure a significant number of compounds which do not exhibit activity against HIV or which are too toxic to administer, making it difficult for the reader to identify the useful compounds.

It has been recognized that drug-resistant variants of HIV can emerge after prolonged treatment with an antiviral agent. Drug resistance most typically occurs by mutation of a gene that encodes for an enzyme used in viral replication, and most typically in the case of HIV, reverse transcriptase, protease, or DNA integrase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous pressures on the virus. One cannot predict, however, what mutations will be induced in the HIV-1 genome by a given drug, whether the mutation is permanent or transient, or how an infected cell with a mutated HIV-1 sequence will respond to therapy with other agents in combination or alternation. This is exacerbated by the fact that there is a paucity of data on the kinetics of drug resistance in long-term cell cultures treated with modern antiretroviral agents.

Ronald Rooke, et al. (Antimicrobial Agents and Chemotherapy, May 1991, p. 988–991) describe the isolation of AZT-resistant variants of HIV-1 from patients on long-term drug therapy by primary isolation of virs in the presence of the drug and by showing that frozen samples of HIV-1, first isolated in the absence of drug pressure, were able to replicate efficiently when AZT was added. Their findings disclose that two isolates of HIV-1 may show susceptability to AZDU.

As more anti-HIV drugs are introduced commercially to treat patients infected with HIV, patients are exposed to a variety of drugs to maintain a low titer of virus during the inevitable resistant patterns that develop. This is true because antiviral drugs alter the selective pressure on the virus population. Any preexisting "resistant" variant has a growth advantage over wild-type competitors. The numbers of resistant virus will increase relative to wild type virus if replication is permitted to proceed. The emergence of viral drug resistance is recognized as a central problem for the success of current antiviral therapy regimens in HIV-infected patients. Patients can ultimately develop multi-drug resistant HIV which is an incalcitrant form of virus that does not exhibit strong sensitivity to a range of anti-HIV drugs. Patients with multi-drug resistant forms of HIV are particularly hard to treat and will become more numerous in the future. It is a current goal of antiviral therapy to identify compounds and methods to treat patients with multi-drug resistant forms of HIV.

It is an object of the present invention to determine the optimal administration of CS-87 for the treatment of HIV, based on the mutation pattern that it induces in HIV-1.

It is another object of the present invention to provide a method and composition that includes CS-87 for the treatment of patients infected with HIV that exhibits advantageous or improved pharmacokinetic, biodistribution, metabolic, resistance or other parameters over administration of CS-87 alone.

It is also an object of the invention to improve the efficacy of CS-87 during short periods of administration and over extended time periods.

It is another object of the invention to assess the sensitivity of HIV-1 to CS-87 in a patient to whom CS-87 has been administered.

It is also an object of this invention to provide a method for treating a patient with a multiple drug resistant form of HIV that includes administering an effective HIV-treatment amount of CS-87 or its prodrug or salt.

It is yet another object of the present invention to provide a method and composition for the treatment of patients infected with HIV in which CS-87 is administered in combination or alternation with a second compound that acts synergistically with CS-87 against the virus.

It is yet another object of the present invention to provide a method and composition for the treatment of patients infected with HIV in which CS-87 is administered in combination or alternation with a second compound that induces a mutation in HIV at a location other than the 70th codon of the reverse transcriptase region of HIV.

It is a further object of the invention to provide pharmaceutical prodrugs and compositions that increase the efficacy of administration of CS-87 for the treatment of patients infected with HIV.

It is another object of the present invention to provide a method and kit for the detection of CS-87 resistant HIV-1.

SUMMARY OF THE INVENTION

It has been discovered that CS-87 induces a transient mutation in HIV-1 at the 70th codon (K to R; i.e., lysine to arginine) of the reverse transcriptase region of the virus. Based on this discovery, a method for treating HIV is provided that includes administering CS-87 or its pharmaceutically acceptable salt or prodrug to a human in need of therapy in combination or alternation with a drug that induces a mutation in HIV-1 at a location other than the 70th codon of the reverse transcriptase region. This invention can be practiced by referring to published mutation patterns for known anti-HIV drugs, or by determining the mutation pattern for a new drug.

It was surprising to discover that the mutation induced by CS-87 is transient. This is unusual and allows for long term therapy with CS-87, as the mutated virus exposed to CS-87 over time is converted back to naive virus, which has an increased sensitivity to the drug.

CS-87 thus can be administered in combination with one or more antiviral agents which do not induce a mutation at the 70th codon of the reverse transcriptase region to achieve an advantageous therapeutic effect against HIV. In some cases, the enhanced therapeutic effect is not attainable by administration of either agent alone. In a preferred but not necessary embodiment, the effect of administration of the two or more agents in combination or alternation is synergistic.

In one preferred embodiment, CS-87 is administered in combination with a protease inhibitor. In particular embodiments, CS-87 is administered in combination or alternation with indinavir (Crixivan), nelfinavir ([3S-[2(2S*, 3*),3-alpha,4-a-beta,8a-beta-]]-N-(1,1-dimethylethyl) decahydro-2-)2-hydroxy-3-[(3-hydroxy-2-methylbenzoyl) amino]-4-(phenylthio)butyl]-3-isoquinolincarboxamide mono-methanesulfonate) (Viracept), saquinavir (Invirase), or 141W94 (amprenavir; (S)-tetrahydrofuran-3-yl-N-[(1S, 2R)-3-[N-[(4-aminophenyl)sulfonyl]-N-isobutylamino]-1-benzyl-2-hydroxypropyl]carbamate; ritonavir or ABT-378 (N-(4(S)-(2-(2,6-dimethylphenoxy)-acetylamino)-3(S)-hydroxy-5-phenyl-1(S)-benzylpentyl)-3-methyl-2-(S)-(2-oxo(1,3-diazaperhydroxinyl)butanamine.

In another preferred embodiment, CS-87 is administered in combination or alternation with a nucleoside analog, including (−) and racemic FTC, 3TC, D4T, DDI, DDC, or abacavir (1592U89) which is (1S,4R)-4-[2-amino-6-cyclopropyl-amino)-9H-purin-9-yl]-2-cyclopentene-1-methanol succinate; or in combinationor alternation with a nucleotide analogue, including adefovir or PMPA.

In another embodiment, CS-87 is administered in combination with a nonnucleoside reverse transcriptase inhibitor such as DMP-266 (efavirenz; 1,4-dihydro-2H-3,1-benzoxazin-2-one); delavirdine, (1-[3-(1-methyl-ethyl) amino]-2-pyridinyl-4-[[5-[(methylsulfonyl)amino]-1H-indol-2-yl]carbonyl]-, monoethanesulfonate), or nevirapine.

In other embodiments, CS-87 is administered in combination or alternation with an HIV-integrase inhibitor or a chemokine inhibitor or a fusion inhibitor.

In general, during alternation therapy, an effective dosage of each agent is administered serially, whereas in combination therapy, an effective dosage of two or more agents are administered together. The dosages will depend on such factors as absorption, biodistribution, metabolism and excretion rates for each drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. Examples of suitable dosage ranges for anti-HIV compounds, including nucleoside derivatives (e.g. D4T, DDI, and 3TC) or protease inhibitors, for example, nelfinavir and indinavir, can be found in the scientific literature and in the Physicians Desk Reference. Many examples of suitable dosage ranges for other compounds described herein are also found in public literature or can be identified using known procedures. These dosage ranges can be modified as desired to achieve a desired result.

The disclosed combination and alternation regiments are useful in the prevention and treatment of HIV infections and other related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be used prophylactically to prevent or retard the progression of clinical illness in individuals who are anti-HIV antibody or HIV-antigen positive or who have been exposed to HIV.

Importantly, it has also been discovered that CS-87 and its prodrugs and pharmaceutically acceptable salts are active (i.e., with an $EC_{50}$ (also referred to herein as $IC_{50}$) that is at most less than five fold the $EC_{50}$ of the drug in wild type virus, and preferably, less than 4, 3, or 2 times the $EC_{50}$ of the drug in wild type virus) against multiple-drug resistant forms of HIV. As used herein, we define multiple drug resistant HIV as having at least one of the following characteristics: (i) the drug resistant strain is genotypically resistant (greater than five fold resistant and more typically, greater than 10, 50 or 100 fold resistant in a same cell line over wild type virus) to AZT and D4T; (ii) the drug resistant strain is genotypically resistant to 3TC and (−) and racemic FTC; (iii) the drug resistant strain is phenotypically resistant (greater than five fold resistant and more typically, greater than 10, 50 or 100 fold resistant in a same cell line over wild type virus) to HIV strains of virus with mutations at the 41, 215 and 184 codons in the reverse transcriptase region, or at least the 184 with at least the 41 or 215 mutations; (iv) the drug resistant strain is genotypically resistant to at least two protease inhibitors; (v) the drug resistant strain is genotypically resistant to at least two protease inhibitors; (vi) the drug resistant strain is genotypically resistant to at least two non nucleoside reverse transcriptase inhibitors; or (vii) the drug resistant strain is genotypically resistant to at least two nucleoside reverse transcriptase inhibitors.

Therefore, in another important embodiment of this invention, a method for treating a patient with a multiple drug resistant form of HIV is provided that includes administering an effective HIV-treatment amount of CS-87 or its prodrug or salt.

In any of the embodiments described herein, if CS-87 is administered in combination or alternation with a second nucleoside or nonnucleoside reverse transcriptase inhibitor that is phosphorylated to an active form, and for example, the active 3'-triphosphate form, by a kinase enzyme, it is preferred that a second compound be phosphorylated by an enzyme that is different from that which phosphorylates CS-87 in vivo, typically thymidine kinase.

Examples of other kinase enzymes are cytosine kinase, guanosine kinase, adenosine kinase, deoxycytidine kinase, 5'-nucleotidase, and deoxyguanosine kinase. For that reason, for example, it is preferred that CS-87 not be administered in combination with AZT or D4T, although the CS-87 can be use as salvage therapy against multiple resistant HIV cell lines that are resistant to AZT or D4T.

DETAILED DESCRIPTION OF THE INVENTION

Figure 1:
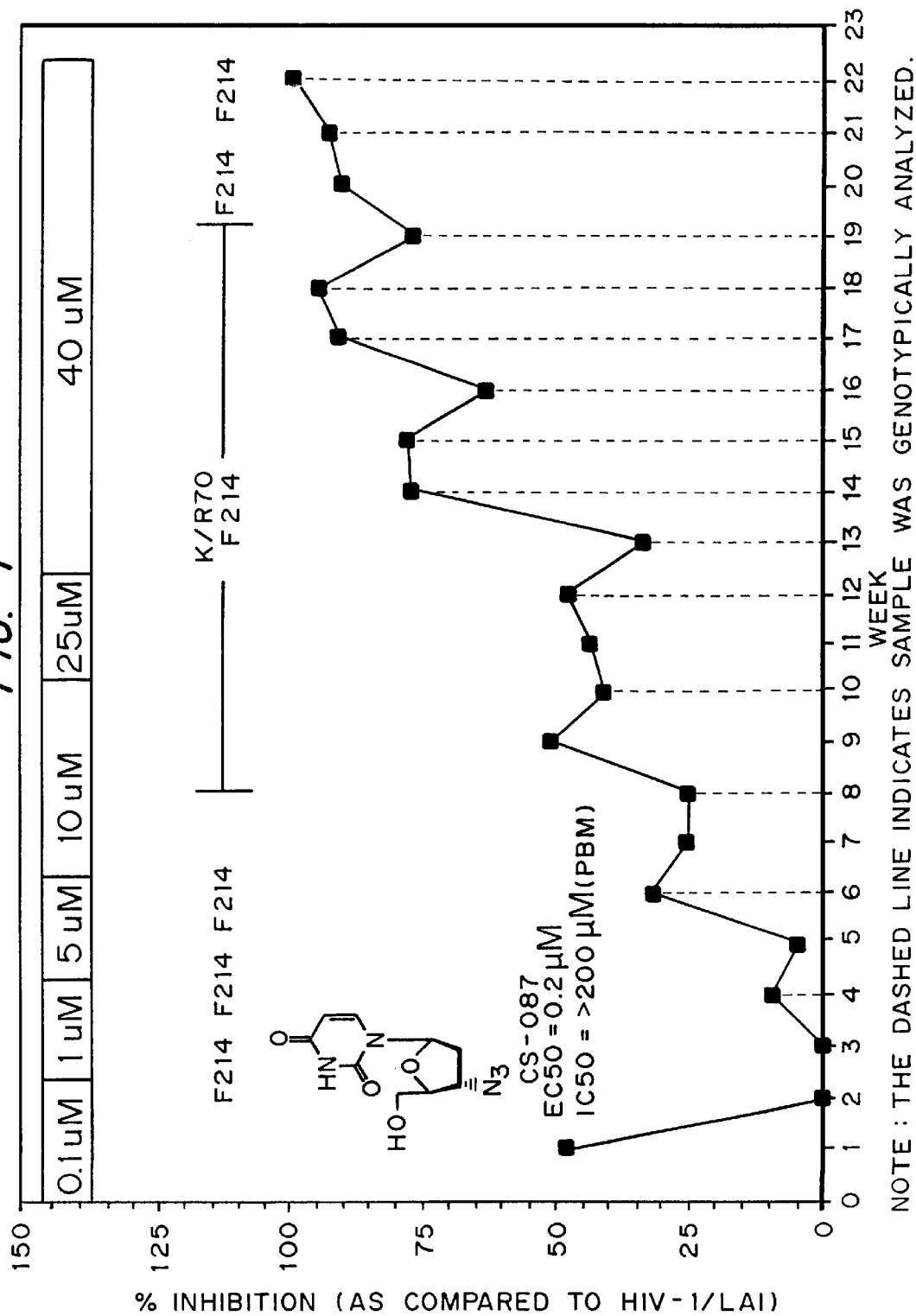
FIG. 1 is a graph of the change in genetic analysis of HIV in the reverse transcriptase region over time as a function of percent inhibition (as compared to HIV-1/LA1) on exposure to increasing concentrations of CS-87.
Figure 2:
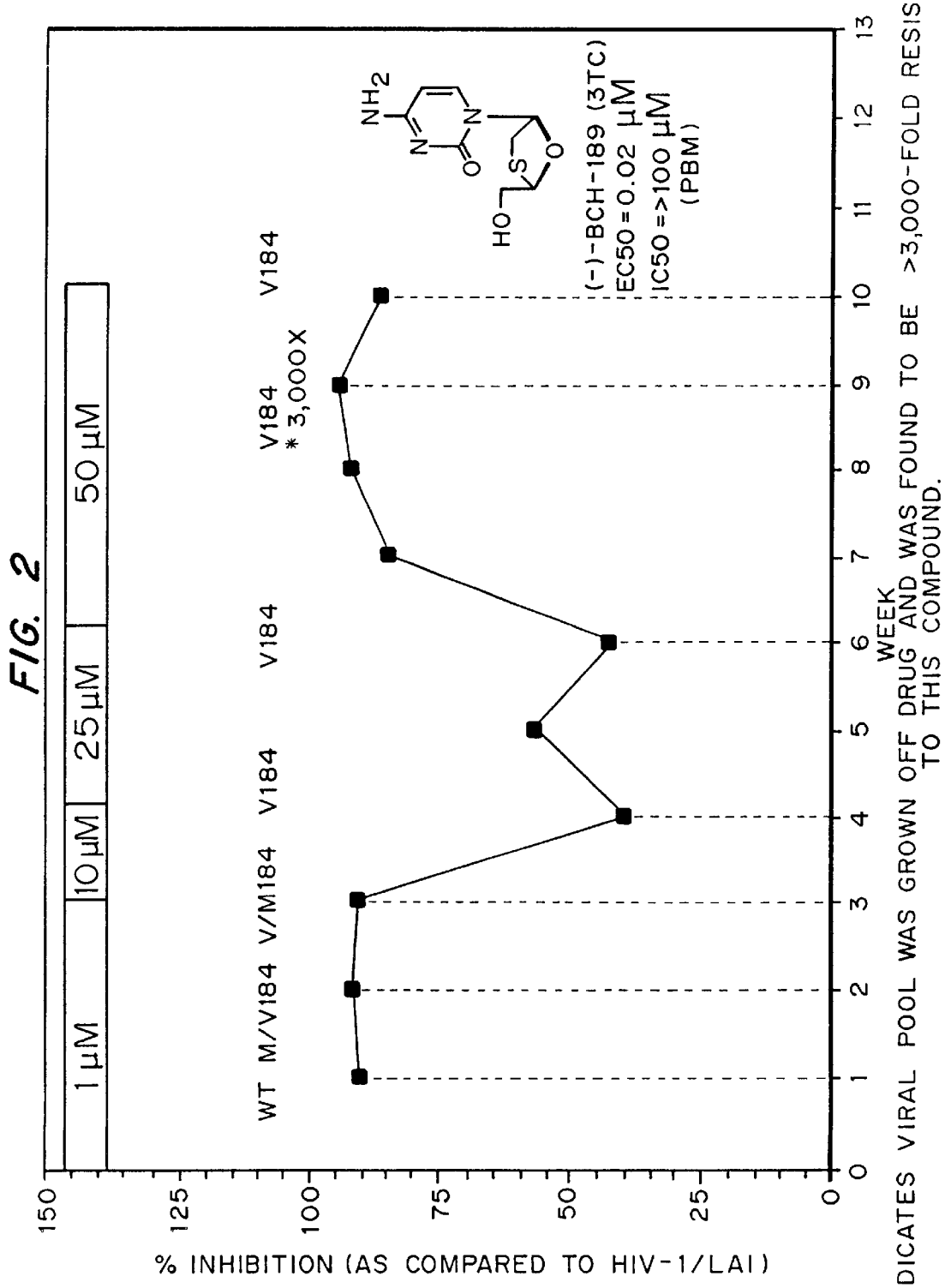
FIG. 2 is a graph of the change in genetic analysis of HIV in the reverse transcriptase region over time as a function of percent inhibition (as compared to HIV-1/LA1) on exposure to increasing concentrations of 3TC.
Figure 3:
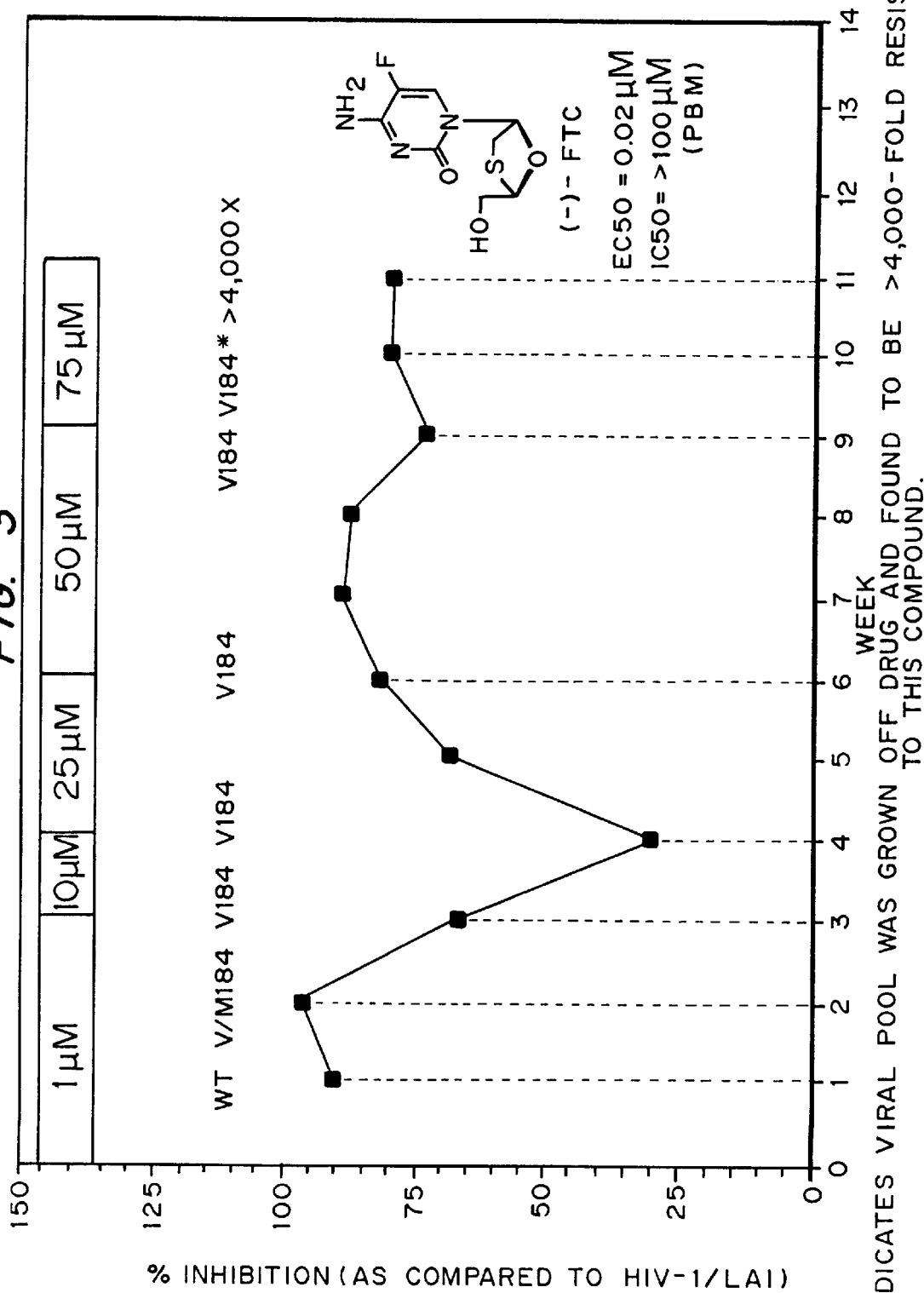
FIG. 3 is a graph of the change in genetic analysis of HIV in the reverse transcriptase region over time as a function of percent inhibition (as compared to HIV-1/LA1) on exposure to increasing concentrations of (−)-cis-FTC.
Figure 4:
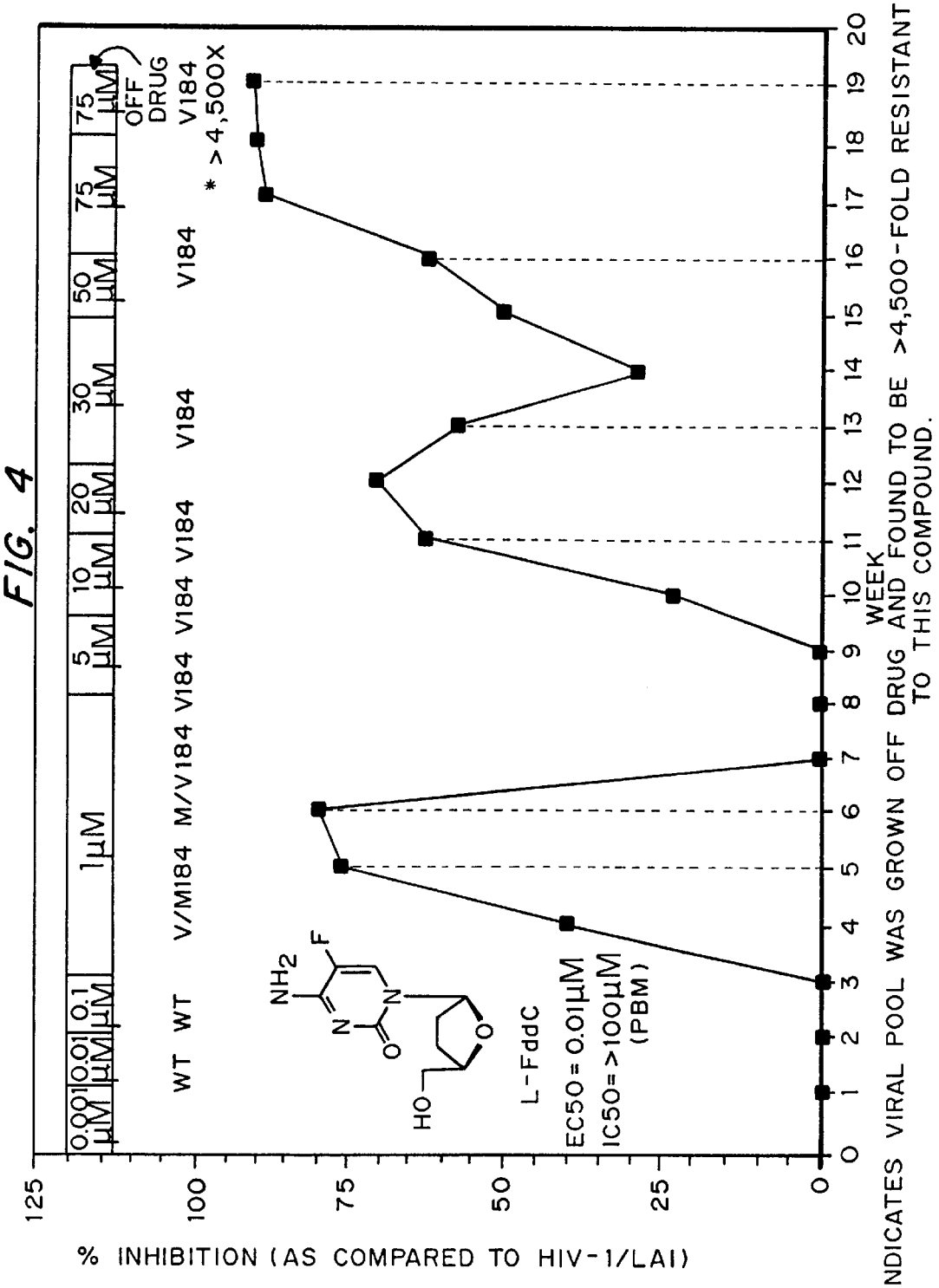
FIG. 4 is a graph of the change in genetic analysis of HIV in the reverse transcriptase region over time as a function of percent inhibition (as compared to HIV-1/LA1) on exposure to increasing concentrations of L-FddC.
Figure 5:
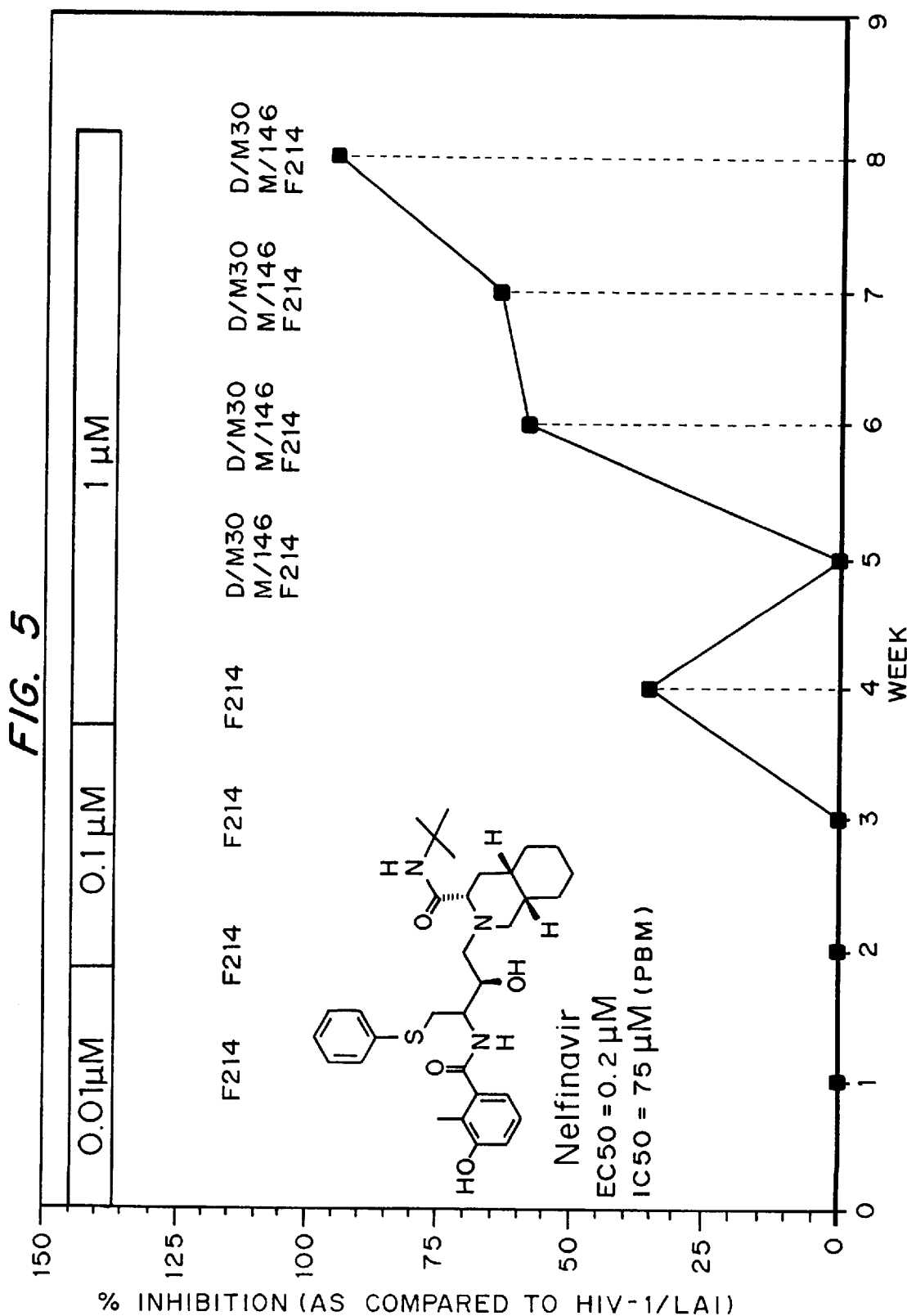
FIG. 5 is a graph of the change in genetic analysis of HIV in the reverse transcriptase region over time as a function of percent inhibition (as compared to HIV-1/LA1) on exposure to increasing concentrations of nelfinavir.
Figure 6:
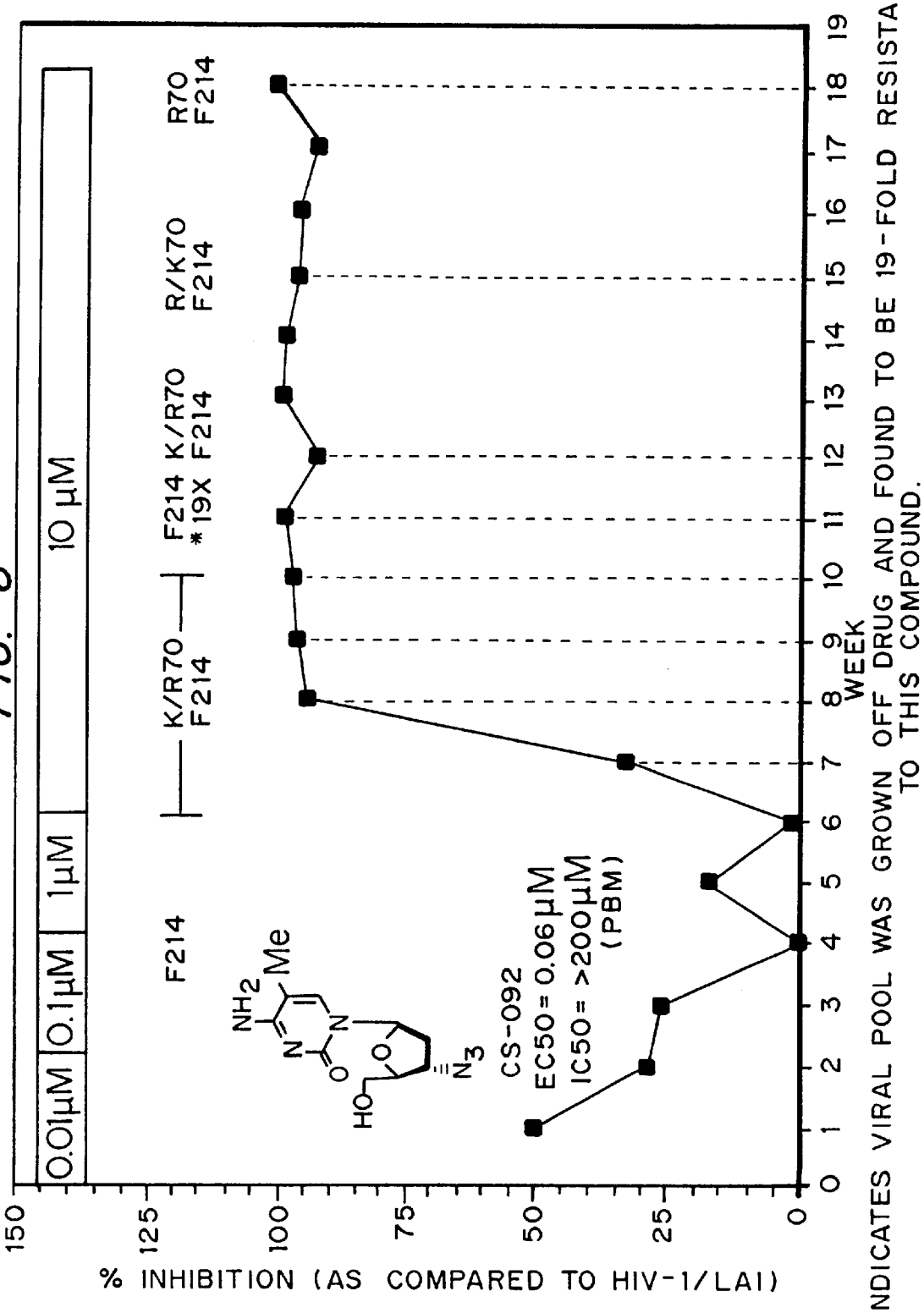
FIG. 6 is a graph of the change in genetic analysis of HIV in the reverse transcriptase region over time as a function of percent inhibition (as compared to HIV-1/LA1) on exposure to increasing concentrations of CS-92.
Figure 7:
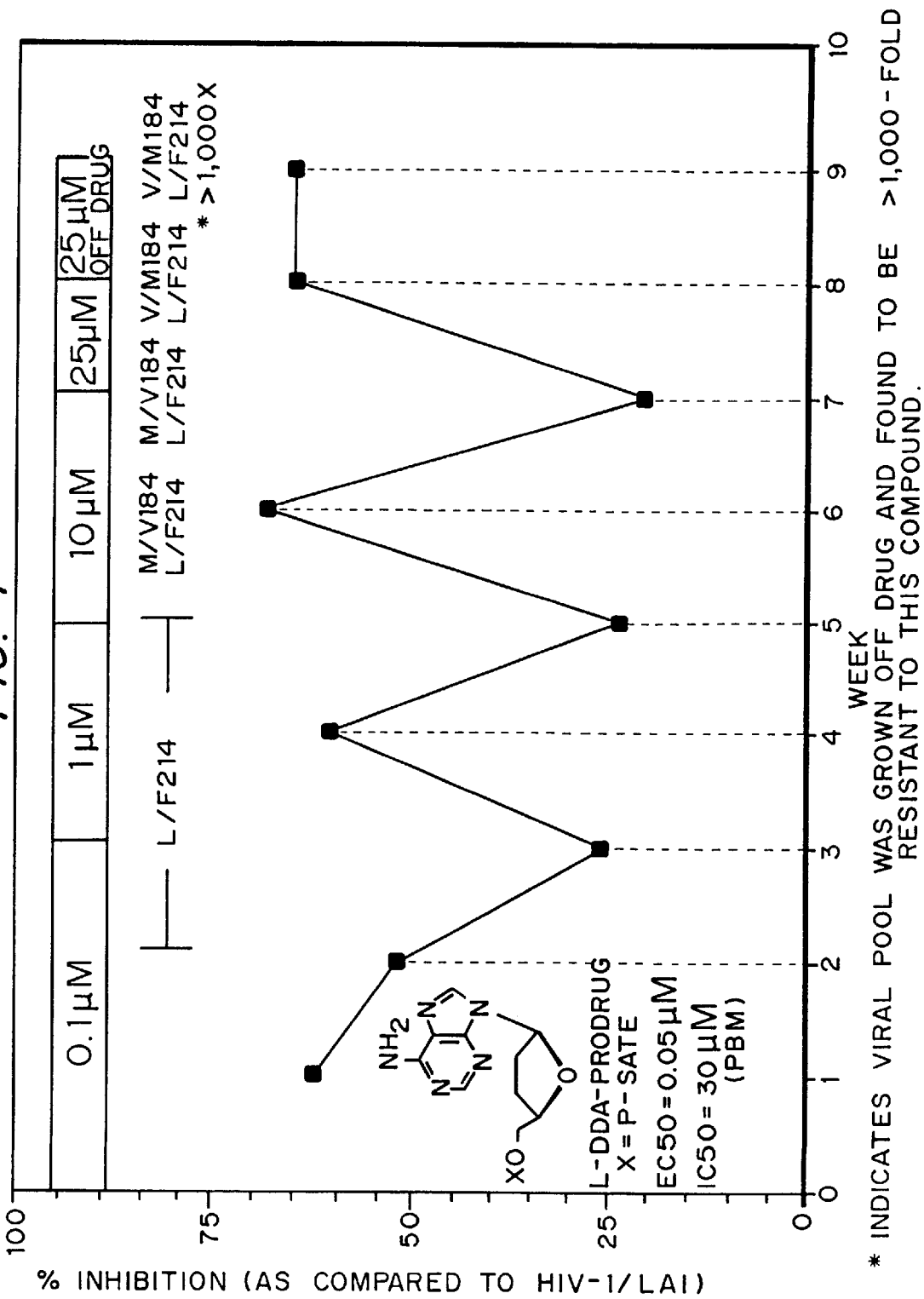
FIG. 7 is a graph of the change in genetic analysis of HIV in the reverse transcriptase region over time as a function of percent inhibition (as compared to HIV-1/LA 1) on exposure to increasing concentrations of an L-DDA stabilized prodrug.
Figure 8:
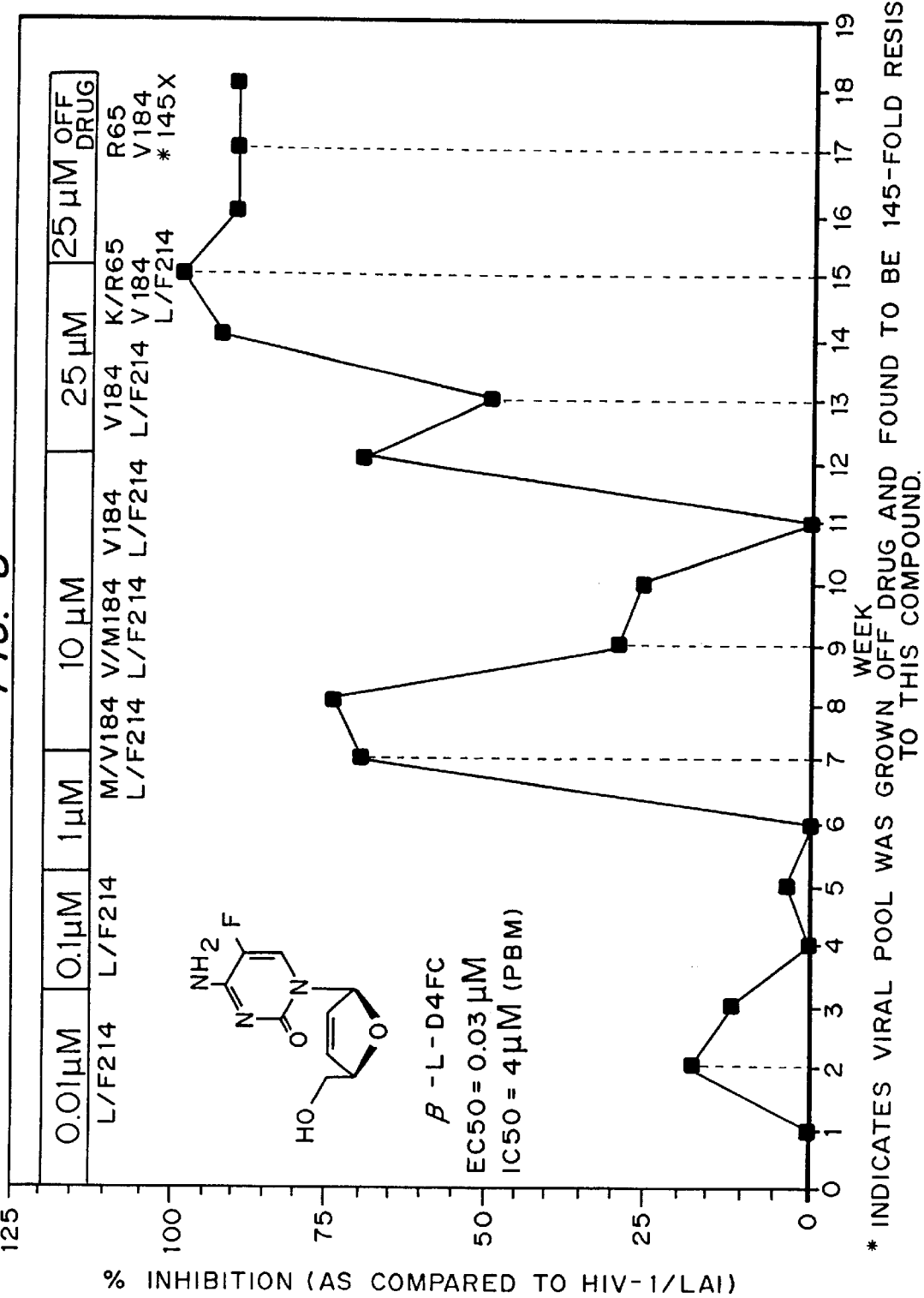
FIG. 8 is a graph of the change in genetic analysis of HIV in the reverse transcriptase region over time as a function of percent inhibition (as compared to HIV-1/LA1) on exposure to increasing concentrations of L-D4FC.
Figure 9:
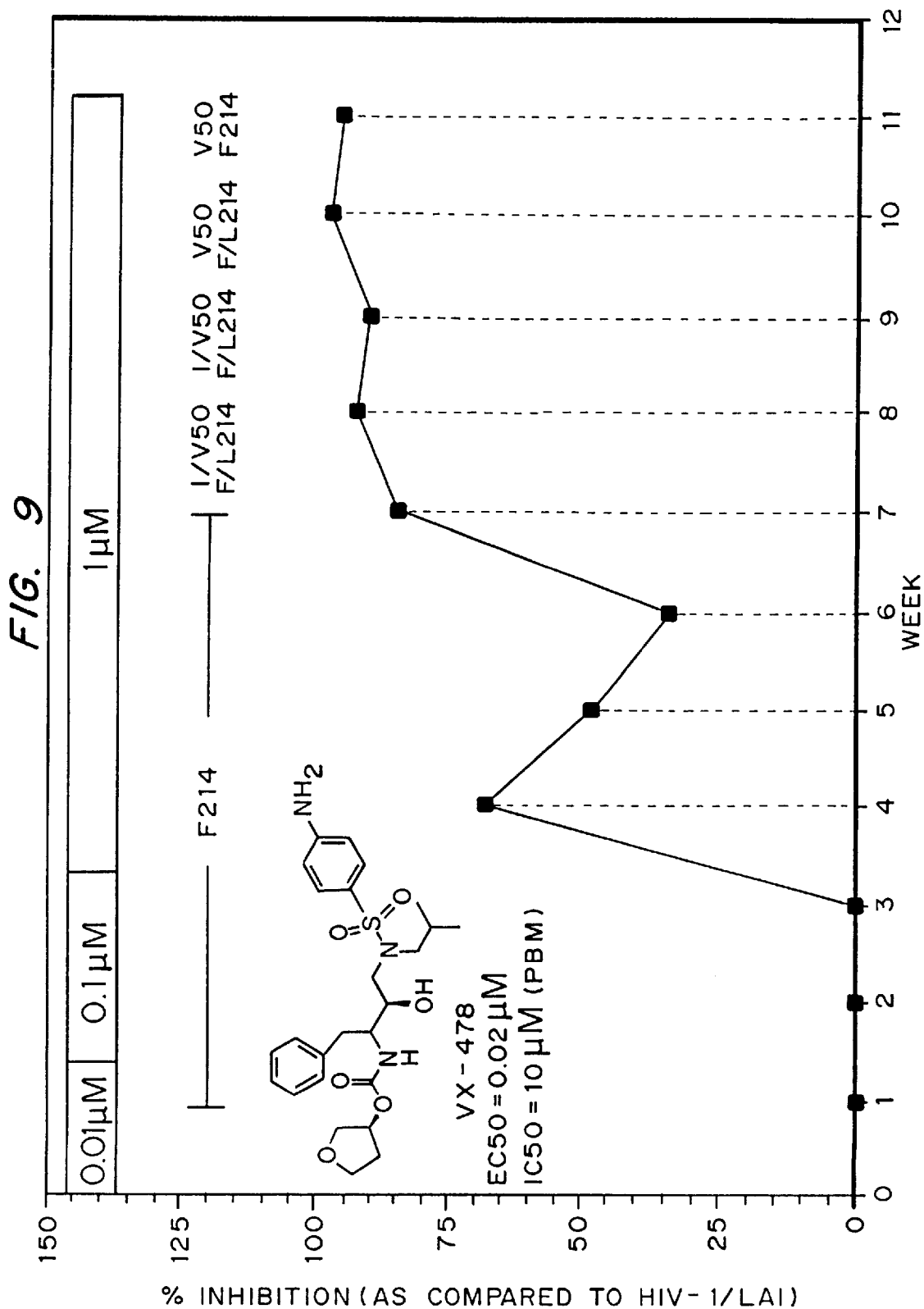
FIG. 9 is a graph of the change in genetic analysis of HIV in the reverse transcriptase region over time as a function of percent inhibition (as compared to HIV-1/LA1) on exposure to increasing concentrations of VX-478.

As used herein, the term "substantially pure" or "substantially in the form of one optical isomer" refers to a nucleoside composition that includes at least 95% to 98%, or more, preferably 99% to 100%, of a single enantiomer of that nucleoside. In a preferred embodiment, CS-87 is administered in substantially pure form for any of the disclosed indications (i.e., in β-D enantiomeric form).

As used herein, the term "prodrug" refers to the 5' and $N^4$ acylated, alkylated, or phosphorylated (including mono, di, and triphosphate esters as well as stabilized phosphates and phospholipid) derivatives of CS-87. In one embodiment, the acyl group is a carboxylic acid ester in which the non-carbonyl moiety of the ester group is selected from straight, branched, or cyclic alkyl, alkoxyalkyl including methoxymethyl, aralkyl including benzyl, a aryloxyalkyl including phenoxymethyl, aryl including phenyl optionally substituted by halogen, alkyl, alkyl or alkoxy, sulfonate esters such as alkyl or aralkyl sulphonyl including methanesulfonyl, trityl or monomethoxytrityl, substituted benzyl, trialkylsilyl, or diphenylmethylsilyl. Aryl groups in the esters optimally comprise a phenyl group. The alkyl group can be straight, branched or cyclic and is preferably C1 to C18.

The abbreviations of amino acids used herein are described in Table 1.

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | GAC | GAU | |
| Glutamic acid | Glu | B | GAA | GAG | | | |
| Phenylalanine | Phe | F | UUC | UUU | | | |
| Clycine | Gly | G | GGA | GCG | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | GUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Senne | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

It has been discovered that CS-87 induces a transient mutation in HIV-1 at the 70th codon (K to R; i.e., lysine to arginine) of the reverse transcriptase region of the virus. Based on this discovery, a method for treating HIV is provided that includes administering CS-87 or its pharmaceutically acceptable salt or prodrug to a human in need of therapy in combination or alternation with a drug that induces a mutation in HIV-1 at a location other than the 70th codon of the reverse transcriptase region. This invention can be practiced by referring to published mutation patterns for known anti-HIV drugs, or by determining the mutation pattern for a new drug.

Importantly, it has also been discovered that CS-87 and its simple prodrugs and pharmaceutically acceptable salts are active against multiple-drug resistant forms of HIV. Therefore, in another important embodiment of this invention, a method for treating a patient with a drug resistant form of HIV is provided that includes administering an effective HIV-treatment amount of CS-87 or its simple prodrug or salt.

This disclosure therefore includes at least the following embodiments.

(i). A method for treating a human infected with HIV comprising administering CS-87 or its pharmaceutically acceptable salt or prodrug in alternation or combination with a second anti-HIV drug that induces a mutation in HIV at a location other than the 70th codon of the reverse transcriptase region of HIV;

(ii). The method of (i), wherein the second anti-HIV drug is a protease inhibitor;

(iii). The method of (ii), wherein the protease inhibitor is indinavir, nelfinavir; saquinavir, ritonavir, ABT-378, or amprenavir.

(iv). The method of (i), wherein the second anti-HIV drug is a nucleoside analogue.

(v). The method of (iv), wherein the nucleoside analogue is (−) and racemic FTC, 3TC, DDC, DDI, D-D4FC, DAPD, FddA, or abacavir.

(vi). The method of (i), wherein the second anti-HIV drug is a non-nucleoside reverse transcriptase inhibitor.

(vii). The method of (vi), wherein the non-nucleoside reverse transcriptase inhibitor is efavirenz, nevirapine, MKC-442, AG-1549, or delavirdine.

(viii). The method of (i), wherein CS-87 is administered in combination or alternation with an HIV-integrase inhibitor or a chemokine inhibitor.

(ix). A method for assessing the sensitivity of HIV-1 to CS-87 in a patient to whom CS-87 has been administered, comprising isolating a sample of HIV-1 from the patient and identifying whether a mutation has occurred at codon 70 in the reverse transcriptase region of the virus.

(x). A method for treating a patient infected with a strain of HIV that is resistant to 3TC comprising administering an effective amount of CS-87 or its pharmaceutically acceptable prodrug or salt to the patient optionally in a pharmaceutically acceptable carrier.

(xi). A method for treating a patient infected with a strain of HIV that is resistant to DDI comprising administering an effective amount of CS-87 or its pharmaceutically acceptable prodrug or salt to the patient optionally in a pharmaceutically acceptable carrier.

(xii). A method for treating a patient infected with a strain of HIV that is resistant to DDC comprising administering an effective amount of CS-87 or its pharmaceutically acceptable prodrug or salt to the patient optionally in a pharmaceutically acceptable carrier.

(xiii). A method for treating a patient infected with a strain of HIV that is resistant to nevirapine comprising administering an effective amount of CS-87 or its pharmaceutically acceptable prodrug or salt to the patient optionally in a pharmaceutically acceptable carrier.

(xiv). A method for treating a patient infected with a strain of HIV that is resistant to delavirdine comprising administering an effective amount of CS-87 or its pharmaceutically acceptable prodrug or salt to the patient optionally in a pharmaceutically acceptable carrier.

(xv). A method for treating a patient infected with a strain of HIV that is resistant to efavirenz comprising administering an effective amount of CS-87 or its pharmaceutically acceptable prodrug or salt to the patient optionally in a pharmaceutically acceptable carrier.

(xvi). A method for treating a patient infected with a strain of HIV that is resistant to Indinavir comprising administering an effective amount of CS-87 or its pharmaceutically acceptable prodrug or salt to the patient optionally in a pharmaceutically acceptable carrier.

(xvii). A method for treating a patient infected with a strain of HIV that is resistant to nelfinavir comprising administering an effective amount of CS-87 or its pharmaceutically acceptable prodrug or salt to the patient optionally in a pharmaceutically acceptable carrier.

(xviii). A method for treating a patient infected with a strain of HIV that is resistant to ritonavir comprising administering an effective amount of CS-87 or its pharmaceutically acceptable prodrug or salt to the patient optionally in a pharmaceutically acceptable carrier.

(xix). A method for treating a patient infected with a strain of HIV that is resistant to saquinavir comprising administering an effective amount of CS-87 or its pharmaceutically acceptable prodrug or salt to the patient optionally in a pharmaceutically acceptable carrier.

(xx). A method for treating a patient infected with a strain of HIV that is resistant to AZT comprising administering an effective amount of CS-87 or its pharmaceutically acceptable prodrug or salt to the patient optionally in a pharmaceutically acceptable carrier.

(xxi). A method for treating a patient infected with a strain of HIV that is resistant to D4T comprising administering an effective amount of CS-87 or its pharmaceutically acceptable prodrug or salt to the patient optionally in a pharmaceutically acceptable carrier.

(xxii). A method for treating a patient infected with a strain of HIV that is resistant to dd4FC comprising administering an effective amount of CS-87 or its pharmaceutically acceptable prodrug or salt to the patient optionally in a pharmaceutically acceptable carrier.

(xxiii). A method for treating a patient infected with a strain of HIV that is resistant to DAPD comprising administering an effective amount of CS-87 or its pharmaceutically acceptable prodrug or salt to the patient optionally in a pharmaceutically acceptable carrier.

(xxiv). A method for treating a patient infected with a strain of HIV that is resistant to FddA comprising administering an effective amount of CS-87 or its pharmaceutically acceptable prodrug or salt to the patient optionally in a pharmaceutically acceptable carrier.

(xxv). A method for treating a patient infected with a strain of HIV that is resistant to (−) and racemic FTC comprising administering an effective amount of CS-87 or its pharmaceutically acceptable prodrug or salt to the patient optionally in a pharmaceutically acceptable carrier.

(xxvi). A method for treating a patient infected with a strain of HIV that is resistant to abacavir comprising administering an effective amount of CS-87 or its pharmaceutically acceptable prodrug or salt to the patient optionally in a pharmaceutically acceptable carrier.

(xxvii). A method for treating a patient infected with a strain of HIV that is resistant to amprenavir comprising administering an effective amount of CS-87 or its pharmaceutically acceptable prodrug or salt to the patient optionally in a pharmaceutically acceptable carrier.

(xxiii). A method for treating a patient infected with a strain of HIV that is resistant to MKC-442 comprising administering an effective amount of CS-87 or its pharmaceutically acceptable prodrug or salt to the patient optionally in a pharmaceutically acceptable carrier.

(xxix). A method for treating a patient infected with a strain of HIV that is resistant to ABT-378 comprising administering an effective amount of CS-87 or its pharmaceutically acceptable prodrug or salt to the patient optionally in a pharmaceutically acceptable carrier.

(xxx). A method for treating a patient infected with a strain of HIV that is resistant to AG-1549 comprising administering an effective amount of CS-87 or its pharmaceutically acceptable prodrug or salt to the patient optionally in a pharmaceutically acceptable carrier.

It has been discovered that CS-87 induces a transient mutation in HIV-1 at the 70th codon (K to R; i.e., lysine to arginine) in the reverse transcriptase region. Based on this discovery, a method for treating HIV is provided that includes administering CS-87 to a human in need of therapy in combination or alternation with a drug that induces a mutation in HIV-1 at a location other than the 70th codon of the reverse transcriptase region. This invention can be practiced by referring to published mutation patterns for known anti-HIV drugs, or by determining the mutation pattern for a new drug.

By practicing the invention described herein, one can increase the effectiveness of therapy of CS-87 by maximizing the sensitivity of the virus to the compound.

I. CS-87 and Related Compounds

In one embodiment, an effective HIV-treatment amount is administered of a compound of the formula:

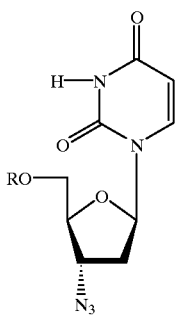

wherein R is hydrogen, acyl or a phosphate ester, including monophosphate, diphosphate, or triphosphate, or a stabilized phosphate ester, or a pharmaceutically acceptable salt thereof. In another embodiment, CS-87 is provided as a lipophilic or hydrophilic prodrug, as discussed in more detail below.

The term acyl refers to moiety of the formula —C(O)R', wherein R' is alkyl, aryl, alkaryl, aralkyl, heteroaromatic, alkoxyalkyl including methoxymethyl; arylalkyl including benzyl; aryloxyalkyl such as phenoxymethyl; aryl including phenyl optionally substituted with halogen, $C_1$ to $C_4$ alkyl or $C_1$ to $C_4$ alkoxy, or the residue of an amino acid.

The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term amino acid includes naturally occurring and synthetic amino acids, and includes but is not limited to, alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl.

The term alkyl, as used herein, unless otherwise specified, refers to a saturated straight, branched, or cyclic, primary, secondary, or tertiary hydrocarbon, typically of $C_1$ to $C_{18}$, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference.

The term lower alkyl, as used herein, and unless otherwise specified, refers to a $C_1$ to $C_4$ saturated straight or branched alkyl group.

The term alkaryl or alkylaryl refers to an alkyl group with an aryl substituent.

The term aralkyl or arylalkyl refers to an aryl group with an alkyl substituent.

The term halo, as used herein, includes chloro, bromo, iodo, and fluoro.

The term heteroaryl or heteroaromatic, as used herein, refers to an aromatic moiety that includes at least one sulfur, oxygen, or nitrogen in the aromatic ring. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, pyridazinyl, pyrazinyl, cinnolinyl, phthalazinyl, quinoxalinyl, xanthinyl, hypoxanthinyl, and pteridinyl. Functional oxygen and nitrogen groups on the heterocyclic base can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl.

The term lipophilic prodrug refers to a nucleoside that contains a covalent substituent at the 5'-hydroxyl position that renders the nucleoside more lipophilic than the parent nucleoside with a 5'-hydroxyl group. A 5'-phosphoether lipid prodrug is a nucleoside that is more lipophilic than the parent drug and which can be cleaved to form a nucleoside 5'-phosphate.

The compound can be converted into a pharmaceutically acceptable ester by reaction with an appropriate esterifying agent, for example, an acid halide or anhydride. The compound or its pharmaceutically acceptable prodrug can be converted into a pharmaceutically acceptable salt thereof in a conventional manner, for example, by treatment with an appropriate base. The ester or salt of the compound can be converted into the parent compound, for example, by hydrolysis.

Any of the compounds described herein for combination or alternation therapy can be administered as any derivative that upon administration to the recipient, is capable of providing directly or indirectly, the parent compound, or that exhibits activity itself. Nonlimiting examples are the pharmaceutically acceptable salts (alternatively referred to as "physiologically acceptable salts"), and a compound which has been alkylated or acylated at an appropriate position. The modifications can affect the biological activity of the compound, in some cases increasing the activity over the parent compound. This can easily be assessed by preparing the derivative and testing its antiviral activity according to known methods.

As used herein, the term pharmaceutically acceptable salts refers to salts that retain the desired biological activity of the herein-identified compounds and exhibit minimal undesired toxicological effects. Non-limiting examples of such salts are (a) acid addition salts formed with inorganic acids (for example, hydrochloric acid, hydrobromic acid, sulfuric acid, phosphoric acid, nitric acid, and the like), and salts formed with organic acids such as amino acid, acetic acid, oxalic acid, tartaric acid, succinic acid, malic acid, ascorbic acid, benzoic acid, tannic acid, palmoic acid, alginic acid, polyglutamic acid, naphthalenesulfonic acid, naphthalenedisulfonic acid, and polygalacturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like.

Prodrug Formulations

CS-87 or any of the nucleosides or other compounds which are described herein for use in combination or alternation therapy with CS-87 or its related compounds can be administered as an acylated prodrug or a nucleotide prodrug, as described in detail below.

Any of the nucleosides described herein or other compounds that contain a hydroxyl or amine function can be administered as a nucleotide prodrug to increase the activity, bioavailability, stability or otherwise alter the properties of the nucleoside. A number of nucleotide prodrug ligands are known. In general, alkylation, acylation or other lipophilic modification of the hydroxyl of the compound or of the mono, di or triphosphate of the nucleoside will increase the stability of the nucleotide. Examples of substituent groups that can replace one or more hydrogens on the phosphate moiety or hydroxyl are alkyl, aryl, steroids, carbohydrates, including sugars, 1,2-diacylglycerol and alcohols. Many are described in R. Jones and N. Bischofberger, *Antiviral Research*, 27 (1995) 1–17. Any of these can be used in combination with the disclosed nucleosides or other compounds to achieve a desire effect.

The active nucleoside or other hydroxyl containing compound can also be provided as an ether lipid (and particularly a 5'-phosphoether lipid for a nucleoside), as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation."*AIDS Res. Hum. Retro Viruses.* 6:491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hosteller, K. Y., D. D. Richman, D. A. Carson, L. M. Stuhmiller, G. M. T. van Wijk, and H. van den Bosch. 1992. "Greatly enhanced inhibition of human 0 immunodeficiency virus type 1 replication in CEM and HT4–6C cells by 3'-deoxythymidine diphosphate dimyristoylglycerol, a lipid prodrug of 3,-deoxythymidine." *Antimicrob. Agents Chemother.* 36:2025.2029; Hostetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituent that can be covalently incorporated into the nucleoside or other hydroxyl or amine containing compound, preferably at the 5'-OH position of the nucleoside or lipophilic preparations, include U.S. Pat. No. 5,149,794 (Sep. 22, 1992, Latvian et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Latvian et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Latvian et al.); U.S. Pat. No. 5,543,390 (Aug. 6, 1996, Latvian et al.); U.S. Pat. No. 5,543,391 (Aug. 6, 1996, Latvian et al.); and U.S. Pat. No. 5,554,728 (Sep. 10, 1996; Basra et al.), all of which are incorporated herein by reference. Foreign patent applications that disclose lipophilic substituent that can be attached to the nucleosides of the present invention, or lipophilic preparations, include WHO 89/02733, WHO 90/00555, WHO 91/16920, WHO 91/18914, WHO 93/00910, WHO 94/26273, WHO 96/15132, EP 0 350 287, EP 93917054.4, and WHO 91/19721.

Nonlimiting examples of nucleotide prodrugs are described in the following references: Ho, D. H. W. (1973) "Distribution of Kinase and deaminase of 1β-D-arabinofuranosylcytosine in tissues of man and muse." *Cancer Res.* 33, 2816–2820; Holy, A. (1993) Isopolar phosphorous-modified nucleotide analogues," In: De Clercq (Ed.), *Advances in Antiviral Drug Design*, Vol. 1, JAI Press, pp. 179–231; Hong, C. I., Nechaev, A., and West, C. R. (1979a) "Synthesis and antitumor activity of 1β-D-arabinofuranosylcytosine conjugates of cortisol and cortisone." *Biochem. Biophys. Rs. Commun.* 88, 1223–1229; Hong, C. I., Nechaev, A., Kirisits, A. J. Buchheit, D. J. and West, C. R. (1980) "Nucleoside conjugates as potential antitumor agents. 3. Synthesis and antitumor activity of 1-(β-D-arabinofuranosyl) cytosine conjugates of corticosteroids and selected lipophilic alcohols." *J. Med. Chem.* 28, 171–177; Hosteller, K. Y., Stuhmiller, L. M., Lenting, H. B. M. van den Bosch, H. and Richman *J. Biol. Chem.* 265, 6112–6117; Hosteller, K. Y., Carson, D. A. and Richman, D. D. (1991); "Phosphatidylazidothymidine: mechanism of antiretroviral action in CEM cells." *J. Biol Chem.* 266, 11714–11717; Hosteller, K. Y., Korba, B. Sridhar, C., Gardener, M. (1994a) "Antiviral activity of phosphatidyl-dideoxycytidine in hepatitis B-infected cells and enhanced hepatic uptake in mice." *Antiviral Res.* 24, 59–67; Hosteller, K. Y., Richman, D. D., Sridhar. C. N. Felgner, P. L. Felgner, J., Ricci, J., Gardener, M. F. Selleseth, D. W. and Ellis, M. N. (1994b) "Phosphatidylazidothymidine and phosphatidyl-ddc: Assessment of uptake in mouse lymphoid tissues and antiviral activities in human immunodeficiency virus-infected cells and in rauscher leukemia virus-infected mice." *Antimicrobial Agents Chemother.* 38, 2792–2797; Hunston, R. N., Jones, A. A. McGuigan, C., Walker, R. T., Balzarini, 3., and DeClercq, E. (1984) "Synthesis and biological properties of some cyclic phosphotriesters derived from 2'-deoxy-5-fluorouridine." *J. Med. Chem.* 27,440–444; Ji, Y. H., Moog, C., Schmitt, G., Bischoff, P. and Luu, B. (1990); "Monophosphoric acid esters of 7-β-hydroxycholesterol and of pyrimidine nucleoside as potential antitumor agents: synthesis and preliminary evaluation of antitumor activity." *J. Med. Chem.* 33 2264–2270; Jones, A. S., McGuigan, C., Walker, R. T., Balzarini, J. and DeClercq, E. (1984) "Synthesis, properties, and biological activity of some nucleoside cyclic phosphoramidates." *J. Chem. Soc. Perkin Trans. I*, 1471–1474; Juodka, B. A. and Smart, J. (1974) "Synthesis of diribonucleoside phosph (P→N) amino acid derivatives." *Coll. Czech. Chem. Comm.* 39, 363–968; Kataoka, S., Imai, J., Yamaji, N., Kato, M., Saito, M., Kawada, T. and Imai, S. (1989) "Alkylated cAMP derivatives; selective synthesis and biological activities." *Nucleic Acids Res. Sym. Ser.* 21, 1–2; Kataoka, S., Uchida, "(cAMP) benzyl and methyl triesters." *Heterocycles* 32, 1351–1356; Kinchington, D., Harvey, J. J., O'Connor, T. J., Jones, B. C. N. M., Devine, K. G., Taylor-Robinson D., Jeffries, D. J. and McGuigan, C. (1992) "Comparison of antiviral effects of zidovudine phosphoramidate and phosphorodiamidate derivatives against HIV and ULV in vitro." *Antiviral Chem. Chemother.* 3, 107–112; Kodama, K., Morozumi, M., Saithoh, K. I., Kuninaka, H., Yosino, H. and Saneyoshi, M. (1989) "Antitumor activity and pharmacology of 1-β-D-arabinofuranosylcytosine-5'-stearylphosphate; an orally active derivative of 1-β-D-arabinofuranosylcytosine." *Jpn. J: Cancer Res.* 80, 679–685; Korty, M. and Engels, J. (1979) "The effects of adenosine- and guanosine 3',5' phosphoric and acid benzyl esters on guinea-pig ventricular myocardium." *Naunyn-Schmiedeberg's Arch. Pharmacol.* 310, 103–111; Kumar, A., Goe, P. L., Jones, A. S. Walker, R. T. Balzarini, J. and DeClercq, E. (1990) "Synthesis and biological evaluation of some cyclic phosphoramidate nucleoside derivatives." *J. Med. Chem,* 33, 2368–2375; LeBec, C., and Huynh-Dinh, T. (1991) "Synthesis of lipophilic phosphate triester derivatives of 5-fluorouridine an arabinocytidine as anticancer prodrugs." *Tetrahedron Lett.* 32, 6553–6556; Lichtenstein, J., Barner, H. D. and Cohen, S. S. (1960) "The metabolism of exogenously supplied nucleotides by *Escherichia coli.*," *J. Biol. Chem.* 235, 457–465; Lucthy, J., Von Daeniken, A., Friederich, J. Manthey, B., Zweifel, J., Schlatter, C. and Benn, M. H. (1981) "Synthesis and toxicological properties of three naturally occurring cyanoepithioalkanes". *Mitt. Geg. Lebensmittelunters. Hyg.* 72, 131–133 (*Chem. Abstr.* 95, 127093); McGigan, C. Tollerfield, S. M. and Riley, P. a. (1989) "Synthesis and biological evaluation of some phosphate triester derivatives of the anti-viral drug Ara." *Nucleic Acids Res.* 17, 6065–6075; McGuigan, C., Devine, K. G., O'Connor, T. J., Galpin, S. A., Jeffries, D. J. and Kinchington, D. (1990a) "Synthesis and evaluation of some novel phosphoramidate derivatives of 3'-azido-3'-deoxythymidine (AZT) as anti-HIV compounds." *Antiviral Chem. Chemother.* 1 107–113; McGuigan, C., O° Connor, T. J., Nicholls, S. R. Nickson, C. and Kinchington, D. (1990b) "Synthesis and anti-HIV activity of some novel substituted dialkyl phosphate derivatives of AZT and ddCyd." *Antiviral Chem. Chemother.* 1, 355–360; McGuigan, C., Nicholls, S. R., O'Connor, T. J., and Kinchington, D. (1990c) "Synthesis of some novel dialkyl phosphate derivative of 3modified nucleosides as potential anti-AIDS drugs." *Antiviral Chem. Chemother.* 1, 25–33; McGuigan, C., Devin, K. G., O'Connor, T. J., and Kinchington, D. (1991) "Synthesis and anti-HIV activity of some haloalkyl phosphoramidate derivatives of 3'-azido-3' deoxythylmidine (AZT); potent activity of the trichloroethyl methoxyalaninyl compound." *Antiviral Res.* 15, 255–263; McGuigan, C., Pathirana, R. N., Balzarini, J. and DeClercq, E. (1 993b) "Intracellular delivery of bioactive AZT nucleotides by aryl phosphate derivatives of AZT." *J. Med. Chem.* 36, 1048–1052.

Alkyl hydrogen phosphate derivatives of the anti-HIV agent AZT may be less toxic than the parent nucleoside analogue. *Antiviral Chem. Chemother.* 5, 271–277; Meyer, R. B., Jr., Shuman, D. A. and Robins, R. K. (1973) "Synthesis of purine nucleoside 3', 5'-cyclic phosphoramidates." *Tetrahedron Lett.* 269–272; Nagyvary, J. Gohil, R. N., Kirchner, C. R. and Stevens, J. D. (1973) "Studies on neutral esters of cyclic AMP," *Biochem. Biophys. Res. Commun.* 55, 1072–1077; Namane, A. Gouyette, C., Fillion, M. P., Fillion, G. and Huynh-Dinh, T. (1992) "Improved brain delivery of AZT using a glycosyl phosphotriester prodrug." *J. Med. Chem.* 35, 3039–3044; Nargeot, J. Nerbonne, J. M. Engels, J. and Leser, H. A. (1983) *Natl. Acad. Sci. U.S.A.* 80, 2395–2399; Nelson, K. A., Bentrude, W. G. Stser, W. N. and Hutchinson, J. P. (1987) "The question of chair-twist equilibria for the phosphate rings of nucleoside cyclic 3', 5' monophosphates. $^1$H NMR and x-ray crystallographic study of the diastereomers of thymidine phenyl cyclic 3', 5'-monophosphate." *J. Am. Chem. Soc.* 109, 4058–4064; Nerbonne, J. M., Richard, S., Nargeot, J. and Lester, H. A. (1984) "New photoactivatable cyclic nucleotides produce intracellular jumps in cyclic AMP and cyclic GMP concentrations." *Nature* 301, 74–76; Neumann, J. M., Hervé, M., Debouzy, J. C., Guerra, F. I., Gouyette, C., Dupraz, B. and Huyny-Dinh, T. (1989) "Synthesis and transmembrane transport studies by NMR of a glucosyl phospholipid of thymidine." *J. Am. Chem. Soc.* 111, 4270–4277; Ohno, R., Tatsumi, N., Hirano, M., Imai, K. Mizoguchi, H., Nakamura, T., Kosaka, M., Takatuski, K., Yamaya, T., Toyama K., Yoshida, T., Masaoka, T., Hashimoto, S., Ohshima, T., Kimura, I., Yamada, K. and Kimura, J. (I 991) "Treatment of myelodysplastic syndromes with orally administered 1-β-D-arabinouranosylcytosine-5' stearylphosphate." *Oncology* 48, 451–455. Palomino, E., Kessle, D. and Horwitz, J. P. (1989) "A dihydropyridine carrier system for sustained delivery of 2',3' dideoxynucleosides to the brain." *J. Med. Chem.* 32, 22–625; Perkins, R. M., Barney, S. Wittrock, R., Clark, P. H., Levin, R. Lambert, D. M., Petteway, S. R., Serafinowska, H. T., Bailey, S. M., Jackson, S., Harnden, M. R. Ashton, R., Sutton, D., Harvey, J. J. and Brown, A. G. (1993) "Activity of BRL47923 and its oral prodrug, SB203657A against a Rauscher murine leukemia virus infection in mice." *Antiviral Res.* 20 (Suppl. I). 84; Piantadosi, C., Marasco, C. J., Jr., Norris-Natschke, S. L., Meyer, K. L., Gumus, F., Surles, J. R., Ishaq, K. S., Kucera, L. S. Iyer, N., Wallen, C. A., Piantadosi, S. and Modest, E. J. (1991) "Synthesis and evaluation of novel ether lipid nucleoside conjugates for anti-HIV-1 activity." *J. Med. Chem.* 34, 1408–1414; Pompon, A., Lefebvre, I., Imbach, J. L., Kahn, S. and Farquhar, D. (1994). "Decomposition pathways of the mono- and bis(pivaloyloxymethyl) esters of azidothymidine-5'-monophosphate in cell extract and in tissue culture medium; an application of the "on-line ISRP-cleaning HPLC technique." *Antiviral Chem Chemother.* 5, 91–98; Postemark, T. (1974) "Cyclic AMP and cyclic GMP." *Annu. Rev. Pharmacol.* 14, 23–33; Prisbe, E. J., Martin, J. C. M., McGhee, D. P. C., Barker, M. F., Smee, D. F. Duke, A. E., Matthews, T. R. and Verheyden, J. P. J. (1986) "Synthesis and antiherpes virus activity of phosphate an phosphonate derivatives of 9-[(1,3-dihydroxy-2-propoxy)methyl] guanine." *J. Med. Chem.* 29, 671–675; Pucch, F., Gosselin, G., Lefebvre, I., Pompon, a., Aubertin, A. M. Dirn, and Imbach, J. L. (1993) "Intracellular delivery of nucleoside monophosphate through a reductase-mediated activation process." *Antiviral Res.* 22, 155–174; Pugaeva, V. P., Klochkeva, S. I., Mashbits, F. D. and Eizengart, R. S. (1969). "Toxicological assessment and health standard ratings for ethylene sulfide in the industrial atmosphere." *Gig. Trf Prof Zabol.* 14, 47–48 (*Chem. Abstr.* 72, 212); Robins, R. K. (1984) "The potential of nucleotide analogs as inhibitors of Retro viruses and tumors." *Pharm. Res.* 11–18; Rosowsky, A., Kim. S. H., Ross and J. Wick, M. M. (1982) "Lipophilic 5'-(alkylphosphate) esters of 1-β-D-arabinofuranosylcytosine and its N$^4$-acyl and 2.2'- anhydro-3'-O-acyl derivatives as potential prodrugs." *J. Med. Chem.* 25, 171–178; Ross, W. (1 961) "Increased sensitivity of the walker turnout towards aromatic nitrogen mustards carrying basic side chains following glucose pretreatment." *Biochem. Pharm.* 8, 235–240;

Ryu, E. K., Ross, R. J. Matsushita, T., MacCoss, M., Hong, C. I. and West, C. R. (1982). "Phospholipid-nucleoside conjugates. 3. Synthesis and preliminary biological evaluation of 1-β-D-arabinofuranosylcytosine 5' diphosphate [-], 2-diacylglycerols." *J. Med. Chem.* 25, 1322–1329; Saffhill, R. and Hume, W. J. (1986) "The degradation of 5-iododeoxyuridine and 5-bromoethoxyuridine by serum from different sources and its consequences for the use of these compounds for incorporation into DNA." *Chem. Biol. Interact.* 57, 347–355; Saneyoshi, M., Morozumi, M., Kodama, K., Machida, J., Kuninaka, A. and Yoshino, H. (1980) "Synthetic nucleosides and nucleotides. XVI. Synthesis and biological evaluations of a series of 1-β-D-arabinofuranosylcytosine 5'-alky or arylphosphates." *Chem*

*Pharm. Bull.* 28,2915–2923; Sastry, J. K., Nehete, P. N., Khan, S., Nowak, B. J., Plunkett, W., Arlinghaus, R. B. and Farquhar, D. (1992) "Membrane-permeable dideoxyuridine 5'-monophosphate analogue inhibits human immunodeficiency virus infection." *Mol. Pharmacol.* 41, 441–445; Shaw, J. P., Jones, R. J. Arimilli, M. N., Louie, M. S., Lee, W. A. and Cundy, K. C. (1994) "Oral bioavailability of PMEA from PMEA prodrugs in male Sprague-Dawley rats." *9th Annual AAPS Meeting.* San Diego, Calif. (Abstract). Shuto, S., Ueda, S., Imamura, S., Fukukawa, K. Matsuda, A. and Ueda, T. (1987) "A facile one-step synthesis of 5' phosphatidiylnucleosides by an enzymatic two-phase reaction." *Tetrahedron Lett.* 28, 199–202; Shuto, S. Itoh, H., Ueda, S., Imamura, S., Kukukawa, K., Tsujino, M., Matsuda, A. and Ueda, T. (1988) *Pharm. Bull.* 36, 209–217. An example of a useful phosphate prodrug group is the S-acyl-2-thioethyl group, also referred to as "SATE".

These compounds can be tested for synergistic activity with CS-87 against HIV according to a number of assays, including those described herein.

II. Analysis of CS-87 Induced Mutation of HIV Genome

From analysis of laboratory samples it appears that the sensitivity of HIV-1 to CS-87 changes over a period of time. It appears that a mutation occurs at only one identified site after a number of weeks of exposure to the drug (lysine to arginine at codon 70 in the reverse transcriptase region), and that the mutant virus after increased pressure from the drug for a number of weeks reverts to wild type virus. The polymorphic change in codon 214 is also observed over time, however, it appears that this change does not affect the amino acid sequence of reverse transcriptase, and thus does not affect the sensitivity of the virus to the drug (see FIG. 1). Methods and kits similar to those described in U.S. Pat. No. 5,409,810 to Larder et al, for AZT, but based on the mutation profile for CS-87, form part of the invention presented herein. In addition to incorporating the Larder patent by reference in its entirety, these techniques are set out below.

In one aspect of the invention there is provided a method of assessing the sensitivity of an HIV-1 sample to CS-87, which includes:

(i) isolating nucleic acid from the sample, (ii) hybridizing an oligonucleotide to the nucleic acid, the oligonucleotide being complementary to a region of the wild-type DNA sequence (or its corresponding RNA) or to a region of the mutant DNA sequence (or its corresponding RNA);

(iii) attempting polymerization of the nucleic acid from the 3'-end of the oligonucleotide, (iv) ascertaining whether or not an oligonucleotide primer extended product is present.

It is possible to use genomic DNA or RNA isolated from HIV-1 samples in this methodology. Suitable cells for supporting the growth of HIV-1 isolate are incubated for a period of time. The cells are recovered by centrifugation. DNA can then be isolated by digestion of the cells with proteinase K in the presence of EDTA and a detergent such as SDS, followed by extraction with phenol.

Well-known extraction and purification procedures are available for the isolation of DNA from a sample. RNA can be isolated using the following methodology. Suitable cells are being infected and incubated for a period of time. The cells are recovered by centrifugation. The cells are resuspended in an RNA extraction buffer followed by digestion using a proteinase digestion buffer and digestion with proteinase K. Proteins are removed in the presence of a phenol/chloroform mixture. RNA can then be recovered following further centrifugation steps. (Maniatis, T., et al, Molecular Coning, A laboratory Manual, 2nd Edition, Cold Spring Harbor Laboratory Press, (1989)).

Although it is possible to use unamplified nucleic acid, due to the relative scarcity of nucleic acid in an HIV-l sample it is preferable to amplify it. Nucleic acid may be selectively amplified using the technique of polymerase chain reaction (PCR), which is an in vitro method for producing large amounts of specific nucleic acid fragment of defined length and sequence from small amounts of a template.

The PCR is comprised of standard reactants using $Mg^2+$ concentration, oligonucleotide primers and temperature cycling conditions for amplification of the RT gene using the primers. The primers are chosen such that they will amplify the entire RT gene or a selected sequence which incorporates nucleotides corresponding to a region of the wild-type DNA sequence of HIV-1 that includes the codon which is mutated.

RNA cannot be amplified directly by PCR. Its corresponding cDNA must be synthesized. Synthesis of cDNA is normally carried out by primed reverse transcription using oligo-dT primers. Advantageously, primers are chosen such that they will simplify the nucleic acid sequence for RT or a selected sequence which incorporates nucleotides corresponding to the region of RNA corresponding to the wild-type DNA sequence or to the region of the mutant DNA sequence corresponding to the 70th codon of the reverse transcriptase region. This could be achieved by preparing an oligonucleotide primer which is complementary to a region of the RNA strand which is upstream of the corresponding sequence of the wild-type DNA sequence. cDNA prepared by this methodology (see Maniatis, T., et al., supra.) can then be used in the same way as for the DNA already discussed.

The next stage of the methodology is to hybridize to the nucleic acid an oligonucleotide which is complementary to a region of the wild-type DNA sequence (or its corresponding RNA) or to a region of the mutant DNA sequence (or its corresponding RNA).

Conditions and reagents are then provided to permit polymerization of the nucleic acid from the 3'-end of the oligonucleotide primer. Such polymerization reactions are well-known in the art.

If the oligonucleotide primer has at its 3'-end a nucleotide which is complementary to a mutant genotype, that is a genotype which has a nucleotide change at the 70th codon in the RT region, then polymerization of the nucleic acid sequence will only occur if the nucleic acid of the sample is the same as the mutant genotype. Polymerization of a wild type nucleic acid sequence will not occur or at least not to a significant extent because of a mis-match of nucleotides at the 3'-end of the oligonucleotide primer and the nucleic acid sequence of the sample.

If the oligonucleotide primer has at its 3'-end of nucleotide which is complementary to the wild-type genotype, that is a genotype which has the wild-type nucleotide at the 70th codon in the RT region, then there will be polymerization of a nucleic acid sequence which is wild-type at that position. There will be no polymerization of a nucleic acid which has a mutant nucleotide at the 3'-position.

The preferred length of each oligonucleotide is 15–20 nucleotides. The oligonucleotide can be prepared according to methodology well known to the man skilled in the art (Koster, H., Drug Research, 30 p. 548 (1980); Koster, H., Tetrahedron Letters p1527 (1972); Caruthers, Tetrahedron Letters, p. 719, (1980); Tetrahedron Letters, p. 1859, (1981); Tetrahedron Letters 24, p245, (1983); Gate. M. Nucleic Acid Research, 8, p. 1081, (1980)) and is generally prepared using an automated DNA synthesizer such as an Applied Biosystems 381 A synthesizer.

It is convenient to determine the presence of an oligonucleotide primer extended product. The means for carrying out the detection is by using an appropriate label.

The label may be conveniently attached to the oligonucleotide primer or to some other molecule which will bind the primer extended polymerization product.

The label may be for example an enzyme, radioisotope or fluorochrome. A preferred label may be biotin which could be subsequently detected using streptavidin conjugated to an enzyme such as peroxidase or alkaline phosphatase. The presence of an oligonucleotide primer extended polymerization product can be detected for example by running the polymerization reaction on an agarose gel and observing a specific DNA fragment labeled with ethidium bromide, or Southern blotted and autoradiographed to detect the presence or absence of bands corresponding to polymerised product. If a predominant band is present which corresponds only to the labeled oligonucleotide then this indicates that polymerization has been occurred. If bands are present of the correct predicted size, this would indicate that polymerization has occurred.

For example, DNA isolated from patients' lymphocytes as described herein is used as a template for PCR amplification using synthetic oligonucleotide primers which either match or mis-match with the amplified sequences. The feasibility of PCR in detecting such mutations has already been demonstrated. PCR using the Amplification Refractory Mutation system ("ARMS") (Newton, C. R., et al. Nucleic Acids Research, 17, p2503, (1989)) Synthetic oligonucleotide are produced that anneal to the regions adjacent to an including the specific mutations such that the 3' ENDE of the oligonucleotide either matches of mismatches with a mutant or wild-type sequence. PCR is carried out which results in the identification of a DNA fragment (using gel electrophoresis) where a match has occurred or no fragment where a mismatch occurred.

DNA is extracted from HIV-1 infected T-cells as described herein and subjected to "ARMS" PCR analysis using these primers.

The presence of a fragment is identified by using an oligonucleotide primer as described above, i.e., by attempting polymerisation using an oligonucleotide primer which may be labelled for the amplified DNA fragment under stringent conditions which only allow hybridisation of complementary DNA (the only difference is that differential hybridisation does not have to be performed as fragments of DNA amplified by the "ARMS" method will be the same whether derived from mutant or wild-type DNS, so a common oligonucleotide can be used to detect the presence of these fragments. The sequence of such an oligonucleotide is derived from a DNA sequence within the DNA fragment that is conserved amongst HIV-1 strains).

The above PCR assay may be adapted to enable direct detection of mutations associated with CS-87 resistance in DNA from PBL samples from infected individuals that have not been cultured to obtain virus. As this material generally contains considerably less HIV-1 DNA than that in infected lymphoid cultures a "double PCR" (or nested set) protocol can be used (Simmonds, P., Balfe, P, Peutherer, J. F., Ludlam, C. A., Bishop, J. O. and Leigh Brown, A. J., J. Virol., 64, 864–872, (1990)) to boost the amount of target HIV-1 RT DNA signal in the samples. The double PCR overcomes the problem of limited amplification of a rare template sequence. A small amount of the pre-amplified material may be used in the second PCR with primer pairs designed to allow discrimination of wild type and mutant residues.

A suitable test kit for use in an assay to determine the resistance status of an HIV-1 sample to CS-87 which makes use of a methodology according to the first aspect of the invention, comprises an oligonucleotide being complementary to a region of the wild-type DNA sequence (or its corresponding RNA) or to a region of the mutant DNA sequence as described herein, other materials required for polymerisation of the nucleic acid from the 3'-end of the oligonucleotide and means for determining the presence of an oligonucleotide primer extended product. Such other materials include appropriate enzymes, buffers and washing solutions, and a label and a substrate for the label if necessary. If PCR is used to amplify nucleic acid then additional materials such as appropriate oligonucleotide primers which will amplify a region of the wild-type DNA sequence (or its corresponding RNA) or a region of the mutant DNA sequence as described herein (or its corresponding RNA) and dNTP's should be included.

In a second aspect of the invention there is provided a method of determining the sensitivity of an HIV-1 sample to CS-87 which comprises:

(i) isolating the nucleic acid from the sample;
(ii) hybridising the nucleic acid with an oligonucleotide being complementary to a region of the wild-type DNA sequence (or its corresponding RNA) or to a region of the mutant DNA sequence set forth in FIG. 1 (or its corresponding RNA) containing one or more of the nucleotides at the region of the 70th codon in the RT region; and
(iii) ascertaining whether or not any of the resulting hybrids of the oligonucleotide and nucleic acid have complementary nucleotides at one of these positions.

Preferably the oligonucleotide is so designed to form a perfectly matched hybrid with its complement.

Nucleic acid (DNA or RNA) is isolated from a sample by the aforementioned methods as described for the first aspect of the invention.

Similarly, PCR may be used to amplify the RT DNA (or its corresponding RNA) or preferably to amplify a region of the RT DNA (or its corresponding RNA) which incorporates DNA (or its corresponding RNA) containing one or more of the nucleotides at the designated position.

In the second stage of this methodology the nucleic acid is then used to hybridize to oligonucleotides complementary to a region of the wild-type DNA sequence (or its corresponding (RNA) or to a region of the mutant DNA sequence. The oligonucleotide may be of any length depending on the number of nucleotide positions of interest which are being examined. If the oligonucleotide is designed to include a nucleotide at only one position of interest then this nucleotide is preferably at or close to the centre position of the oligonucleotide.

In order to ascertain whether or not the oligonucleotide and nucleic acid sequence have formed a matched hybrid, specific hybridisation conditions are set so that a hybrid is only formed when the nucleotide or nucleotides at the 70th codon of the reverse transcriptase region are complementary to the corresponding nucleotide or nucleotides of the oligonucleotide which either permits hybridisation or no hybridisation. It is important to establish for example the temperature of the reaction and the concentration of salt solution before carrying out the hybridisation step to find conditions that are stringent enough to guarantee specificity (Maniatis, T., et al., Molecular Cloning, A Laboratory Manual, 2nd edition, Cold Spring Harbour Laboratory Press, (1989). If the oligonucleotide probe has a DNA sequence which is complementary to a wild-type nucleic acid sequence at one or more of its nucleotides corresponding to the 70th codon in the reverse transcriptase region then this oligonucleotide will hybridize perfectly to wild-type nucleic acid. If there is no hybridize perfectly to wild-type nucleic acid. If there is no hybridisation then this would suggest that the nucleic acid isolated from the same contains one or more mutations.

If the oligonucleotide probe has a DNA sequence which is complementary to a mutant nucleic acid sequence then this oligonucleotide will hybridize to mutant nucleic acid. If there is no hybridisation this would suggest that the nucleic acid isolated from the sample contains no such mutation or mutations. The oligonucleotide probes may be labeled as a means of detection as for the first aspect of the invention.

The hybridisation and subsequent removal of non-hybridised nucleic acids are performed under stringent conditions which only allow hybridization of the complementary DNA and not the oligonucleotide containing a mismatch (i.e. oligonucleotide specific hybridization as described for the detection of sickle cell mutation using the β-globin or HLA-DQα gene (Saikt, R. K., et al., Nature, 324, p163, (1986), the activated Ras gene (Ver Laan-de, Vries, M., et al., Gene, 50, 313, (1986)) and β-thalassaemia Wong, C., et al., Nature, 330, p384, (1987)).

The hybridisation may be carried out by immobilisation of the RT nucleic acid sequence onto nitrocellulose, nylon or other solid matrix (eg. dot-blot). It is convenient to determine the presence of an hybrid by using the means of a label. For example, the chemically synthesized oligonucleotide probes can be suitably labeled using enzyme, radioisotope or fluorochrome. A preferred label may be biotin which could be subsequently detected using streptavidin conjugated to an enzyme such as peroxidase or alkaline phosphatase.

Alternatively the hybridisation may be carried out by immobilisation of the chemically synthesised oligonucleotides referred to above, which are unlabeled, onto a solid support referred to above and subsequent hybridisation by a labeled RT nucleic acid sequence as described previously.

In both situations described above for hybridisation suitable control reactions will be incorporated to determine that efficient hybridisation has occurred. (eg, the hybridisation of oligonucleotides to a complementary oligonucleotide).

Results would be readily interpreted as the isolated nucleic acid would hybridize to either the wild type oligonucleotide or the mutant oligonucleotide.

A suitable test kit for use in an assay to determine the sensitivity of an HIV-1 sample to CS-87 which makes use of a methodology according to the second aspect of the invention comprises an oligonucleotide being complementary to a region of the wild-type DNA sequence (or its corresponding RNA) or to the pertinent region of the mutant DNA sequence, along with other materials required to permit hybridisation. Such materials include appropriate buffers and washing solutions and a label and a substrate for the label if necessary. Normally the oligonucleotide would be labeled. If PCR is used to amplify nucleic acid prior to hybridisation then additional materials such as appropriate oligonucleotide primers which will amplify a region of the wild-type DNA sequence (or its corresponding RNA) or a region of the mutant DNA sequence, appropriate enzymes and dNTP's (deoxy nucleotide triphosphates) should be included.

In one alternate format of the assay, the dNTP's in the amplification may or may not be coupled to a detector molecule such as a radioisotope, biotin, fluorochrome or enzyme.

It is also possible to detect zidovudine resistant mutations in the HIV-1 RT RNA isolated from clinical samples using an RNA amplification system. Using the methodology described by Guatelli et al. (Proc. Natl. Acad. Sci, (USA), 8/7, 1874–1878, (March 1990)) a target nucleic acid sequence can be replicated (amplified) exponentially in vitro under isothermal conditions by using three enzymatic activities essential to retroviral replication: reverse transcriptase, RNase H and a DNA-dependant RNA polymerase. Such a methodology may be employed followed by an hybridisation step to distinguish mutant from wild-type nucleotides at discussed previously.

III. Combination or Alternation Therapy

It has been recognized that drug-resistant variants of HIV can emerge after prolonged treatment with an antiviral agent. Drug resistance most typically occurs by mutation of a gene that encodes for an enzyme used in the viral replication cycle, and most typically in the case of HIV, in either the reverse transcriptase or protease genes. It has been demonstrated that the efficacy of a drug against HIV infection can be prolonged, augmented, or restored by administering the compound in combination or alternation with a second, and perhaps third, antiviral compound that induces a different mutation(s) from that selected for by the principle drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

It has now been discovered that CS-87 induces a transient mutation in HIV-1 at the 70th codon (K to R; i.e., lysine to arginine) in the reverse transcriptase region. Based on this discovery, a method for treating HIV is provided that includes administering CS-87 or its pharmaceutically acceptable salt or prodrug to a human in need of therapy in combination or alternation with a drug that induces a mutation in HIV-1 at a location other than the 70th codon of the reverse transcriptase region.

The second antiviral agent for the treatment of HIV, in one embodiment, can be a protease inhibitor, a reverse transcriptase inhibitor (a "RTI"), which can be either a synthetic nucleoside (a "NRTI") or a non-nucleoside compound (a "NNRTI"), and HIV-integrase inhibitor, or a chemokine inhibitor. In other embodiments, the second (or third) compound can be a pyrophosphate analog, or a fusion binding inhibitor. A list compiling resistance data collected in vitro and in vivo for a number of antiviral compounds is found in Schinazi et al., Mutations in retroviral genes associated with drug resistance, *International Antiviral News*, Volume 5 (8), International Medical Press 1997.

The activity and cytotoxicity of a combination of 3'-azido-2',3'-dideoxyuridine with other nucleoside and non-nucleoside RT inhibitors including ZDV, DAPD, 3TC, Sustiva, Nevirapine, Indinavir, ddI and D-D4FC are being tested using the multiple drug effect analysis and confidence interval method of Belen'kii and Schinazi (Belen'kii, M. S. & Schinazi, R. S. (1994) *Antiviral Research* 25, 1–11). The median effective concentration and combination index (CI) values for 3'-azido-2',3'-dideoxyuridine in combination with several of these drugs in acutely infected human PBMC are shown in Table 2, Table 3, Table 3A, and Table 3B.

The combination of 3'-azido-2',3'-dideoxyuridine and 3TC at a ratio of 100:1 was synergistic at 50%, 75%, 90% and 95% effect levels.

TABLE 2

Combination Antiviral Activity for 3'-azido-2',3'-dideoxyuridine with 3TC in Human PBMC

| Treatment | Parameter[a] | | | | C.I. at $F_a$[b] of | | | |
|---|---|---|---|---|---|---|---|---|
| (drug ratio) | m ± SE | $EC_{50}$ (μM) | $EC_{90}$ (μM) | r | 0.50 | 0.75 | 0.90 | 0.95 |
| AZT | 1.04 ± 0.30 | 0.0016 | 0.013 | 0.96 | | | | |
| NV-01 | 1.62 ± 0.13 | 1.53 | 5.92 | 0.99 | | | | |
| 3TC | 1.08 ± 0.15 | 0.0067 | 0.051 | 0.98 | | | | |
| NV-01 + 3TC (100:1) | 0.06 ± 0.07 | 0.029 | 0.81 | 0.98 | 0.06 ± 0.0074<br>0.06 ± 0.0071 | 0.14 ± 0.03<br>0.13 ± 0.02 | 0.32 ± 0.10<br>0.29 ± 0.09 | 0.57 ± 0.27<br>0.51 ± 0.21 |

[a]m is the slope ± S.E >, EC50 is the median effective concentration, and r is the correlation coefficient, as determined from the median effect plot.
[b]C.I. <1, equal to 1 or >1 indicates synergy, additivity and antagonism, respectively. $F_a$ is a component of the median effect equation referring to the fractin of the system affected (e.g., 0.50 means the C.I. at a 50% reducton of RT activity). C.I. values were determined for a mutually non-exclusive interaction (values in italics are for mutually exclusive interaction, which is less rigorous)

The combination of 3'-azido-2',3'-dideoxyuridine with DAPD at a 1:1 ratio was synergistic at all effect levels. The data were significant at 50%, 75%, and 90% inhibition. The interaction was additive to synergistic at 95% inhibition.

TABLE 3

Combination Antiviral Activity for 3'-Azido-2',3'-dideoxyuridine with DAPD in Human PBMC

| Treatment | Parameter[a] | | | | C.I. at $F_a$[b] of | | | |
|---|---|---|---|---|---|---|---|---|
| (drug ratio) | m ± SE | $EC_{50}$ (μM) | $EC_{90}$ (μM) | r | 0.50 | 0.75 | 0.90 | 0.95 |
| AZT | 0.72 ± 0.18 | 0.001 | 0.021 | 0.94 | | | | |
| NV-01 | 1.50 ± 0.33 | 1.61 | 7.0 | 0.98 | | | | |
| DAPD | 1.40 ± 0.14 | 1.81 | 8.68 | 0.99 | | | | |
| NV-01 + DAPD (1:1) | 1.38 ± 0.25 | 0.88 | 4.36 | 0.97 | 0.59 ± 0.20<br>0.52 ± 0.211 | 0.61 ± 0.24<br>0.54 ± 0.30 | 0.64 ± 0.35<br>0.56 ± 0.48 | 0.66 ± 0.50<br>0.58 |

[a]m is the slope ± S.E >, $EC_{50}$ is the median effective concentration, and r is the correlation coefficient, as determined from the median effect plot.
[b]C.I. <1, equal to 1 or >1 indicates synergy, additivity and antagonism, respectively. $F_a$ is a component of the median effect equation referring to the fraction of the system affected (e.g., 0.50 means the C.I. at a 50% reduction of RT activity). C.I. values were determined for a mutually non-exclusive interaction (values in italics are for mutually exclusive interaction, which is less rigorous).
Note: With exception of AZT, all values for Parameter data are averages of duplicate tests.

TABLE 3A

Combination Antiviral Activity for 3'-Azido-2',3'-dideoxyuridine with Indinavir and JPS-783 in Human PBMC

| Treatment | Parameter[a] | | | | C.I. at $F_a$[b] of | | | |
|---|---|---|---|---|---|---|---|---|
| (drug ratio) | m ± SE | $EC_{50}$ (μM) | $EC_{90}$ (μM) | r | 0.50 | 0.75 | 0.90 | 0.95 |
| AZT | 1016 ± 0.03 | 0.0022 | 0.014 | 0.99 | | | | |
| Novuridine | 1.01 ± 0.01 | 0.19 | 1066 | 0.99 | | | | |
| CS-87 | | | | | | | | |
| Indinavir | 0.86 ± 0.17 | 0.0015 | 0.019 | 0.96 | | | | |
| JPS-783 | 0.91 ± 0.08 | 0.047 | 0.52 | 0.99 | | | | |
| Novuridine + JPS-783 1:1 | 0.64 ± 0.09 | 0.0024 | 0.074 | 0.97 | 0.032 ± 0.021<br>0.032 ± 0.020 | 0.055 ± 0.036<br>0.055 ± 0.033 | 0.095<br>0.094 ± 0.0855 | 0.14<br>0.14 |
| Novuridine + JPS-783 1:5 | 0.71 ± 0.09 | 0.0061 | 0.13 | 0.98 | 0.115 ± 0.055<br>0.114 ± 0.052 | 0.162 ± 0.072<br>0.161 ± 0.068 | 0.2310.120<br>0.228 ± 0.113 | 0.294 ± 0.195<br>0.289 ± 0.178 |
| Novuridine + Indinavir 5:1 | 0.71 ± 0.12 | 0.0025 | 0.055 | 0.96 | 0.030 ± 0.085<br>0.030 ± 0.085 | 0.395 ± 0.102<br>0.395 ± 0.102 | 0.524 ± 0.136<br>0.524 ± 0.136 | 0.637 ± 0.179<br>0.637 ± 0.179 |

TABLE 3A-continued

Combination Antiviral Activity for 3'-Azido-2',3'-dideoxyuridine
with Indinavir and JPS-783 in Human PBMC

| Treatment | Parameter[a] | | | | C.I. at $F_a$[b] of | | | |
|---|---|---|---|---|---|---|---|---|
| (drug ratio) | m ± SE | $EC_{50}$ (μM) | $EC_{90}$ (μM) | r | 0.50 | 0.75 | 0.90 | 0.95 |
| Novuridine + Indinavir 50:1 | 1047 ± 0.18 | 0.18 | 0.84 | 0.99 | 5.70 *5.70* | 3.15 *3.15* | 1.80 ± 1.70 *1.80 ± 1.70* | 1.26 ± 0.65 *1.26 ± 0.65* |

[a]m is the slope ± S.E >, $EC_{50}$ is the median effective concentration, and r is the correlation coefficient, as determined from the median effect plot.
[b]C.I. <1, equal to 1 or >1 indicates synergy, additivity and antagonism, respectively. $F_a$ is a component of the median effect equation referring to the fractin of the system affected (e.g., 0.50 means the C.I. at a 50% reduction of RT activity). C.I. values were determined for a mutually non-exclusive interaction (values in italics are for mutually exclusive interaction, which is less rigorous).
Note: Experiment was conducted in duplicate in T25 flasks.

TABLE 3B

Effects of Novuridine (CS-087), Indinavir (RS-253) and JPS-783 alone
and in combination at ratios 1:1, 1:5, 5:1, and 50:1 on
HIV-1 replication in human PBM cells (day 6)

| Treatment | Concentration (mM) | Inhibition % | $EC_{50}$ (mM) | $EC_{90}$ (mM) |
|---|---|---|---|---|
| AZT | 0.0001 | −12.9* | 0.0022 | 0.014 |
| | 0.001 | 67.6* | | |
| | 0.01 | 83.2* | | |
| | 0.1 | 98.2* | | |
| Novuridine (CS-087) | 0.01 | 34.5* | 0.19 | 1.66 |
| | 0.1 | 32.0* | | |
| | 1 | 87.3* | | |
| | 10 | 98.0* | | |
| Indinavir (RS-253) | 0.001 | 29.9* | 0.0015 | 0.019 |
| | 0.01 | 88.7* | | |
| | 0.1 | 98.8* | | |
| | 1 | 99.3* | | |
| JPS-783 | 0.01 | 24.3* | 0.047 | 0.52 |
| | 0.1 | 55.4* | | |
| | 1 | 95.0* | | |
| | 10 | 99.3* | | |
| CS-087 + JPS-783 1:1 | 0.01 + 0.0001 | 27.6* | 0.0024 | 0.074 |
| | 0.001 + 0.001 | 40.6* | | |
| | 0.01 + 0.01 | 65.9* | | |
| | 0.1 + .01 | 92.6* | | |
| | 1 + 1 | 99.3* | | |
| | 10 + 10 | 98.6* | | |
| CS-087 + JPS-783 1:5 | 0.0001 + 0.0005 | 27.1* | 0.0061 | 0.13 |
| | 0.001 + 0.005 | 37.5* | | |
| | 0.01 + 0.05 | 78.2* | | |
| | 0.1 + 0.5 | 94.5* | | |
| | 1 + 5 | 99.6* | | |
| CS-087 + Indinavir 5:1 | 0.0005 + 0.0001 | 36.4* | 0.0025 | 0.055 |
| | 0.005 + 0.001 | 56.5* | | |
| | 0.05 + 0.01 | 79.8* | | |
| | 0.5 + 0.1 | 99.3* | | |
| | 5 + 1 | 99.5* | | |
| CS-087 + Indinavir 50:1 | 0.0005 + 0.00001 | −45.2 | 0.18 | 0.84 |
| | 0.005 + 0.0001 | −29.2* | | |
| | 0.05 + 0.001 | 7.2* | | |
| | 5 + 0.1 | 99.4* | | |
| | 50 + 1 | 99.5 | | |

The activity of uninfected PBM cells was 1,163 CPM/ml.
All values are corrected for the mean value of the blanks (96 CPM).
The mean value of RT activity in infected cells was 203,207 CPM/ml
The experiment was conducted in duplicate in T25 flasks
*Asterisks indicate data points used in the calculation of $EC_{50}$ $EC_{90}$ In preferred embodiments, CS-87 is administered in combination or alternation with (−) and racemic FTC (2',3'-dideoxy-3'-thia-5-fluorocytidine); 141 W94 (amprenavir, GlaxoWellcome, Inc.); Viramune (nevirapine), Rescriptor (delavirdine); DMP-266 (efavirenz), DDI (2',3'-dideoxyinosine); 3TC (3'-thia-2',3'-dideoxycytidine); or DDC (2',3'-dideoxycytidine). In another preferred embodiment, CS-87 is administered in combination or alternation with abacavir (1592U89), which is (1S,4R)-4-[2-amino-6-cyclopropyl-amino)-9H-purin-9-yl]-2-cyclopentene-1-methanol succinate, or D4T.

Other examples of antiviral agents that can be used in combination or alternation with the compounds disclosed herein for HIV therapy include 3TC; foscarnet; carbovir, acyclovir, interferon, stavudine, and β-D-dioxolane nucleosides such as β-D-dioxolanylguanine (DXG), β-D-dioxolanyl-2,6-diaminopurine (DAPD), and β-D-dioxolanyl-6-chloropurine (ACP).

Preferred protease inhibitors include indinavir ({1(1,S,2R),5(S)]-2,3,5-trideoxy-N-(2,3-dihydro-2-hydroxy-1H-inden-1-yl)-5-[2-[[(1,1-dimethylethyl)amino]carbonyl]-4-(3-pyridinylmethyl)-1-piperazinyl]-2-(phenylmethyl)-D-erythro-pentoamide sulfate; Merck), nelfinavir (Agouron), ritonavir (Abbott), saquinavir (Roche) and DMP-450 {[4R-4(r-a,5-a,6-b,7-6)]-hexahydro-5,6-bis(hydroxy)-1,3-bis(3-amino)phenyl]methyl)-4,7-bis(phenylmethyl)-2H-1,3-diazepin-2-one}-bismesylate (Triangle Pharmaceuticals, Inc.).

Nonlimiting examples of other compounds that can be administered in combination or alternation with CS-87 to augment the properties of the drug on administration include abacavir: (1 S,4R)-4-[2-amino-6-cyclopropyl-amino)-9H-purin-9-yl]-2-cyclopentene-1-methanol succinate (1592U89, a carbovir analog; GlaxoWellcome); BILA 1906: N-{1S-[[[3-[2S-{(1,1-dimethylethyl)amino]carbonyl} -4R-] 3-pyridinylmethyl)thio]-1-piperidinyl]-2R-hydroxy-1S-(phenylmethyl)propyl]amino]carbonyl]-2-methylpropyl}-2-quinolinecarboxamide (Bio Mega/Boehringer-Ingelheim); BILA 2185: N-(1,1-dimethylethyl)-1-[2S-[[2-2,6-dimethylphenoxy)-1-oxoethyl]amino]-2R-hydroxy-4-phenylbutyl]4R-pyridinylthio)-2-piperidinecarboxamide (Bio Mega/Boehringer-Ingelheim); BM+51.0836:triazoloisoindolinone derivative; BMS 186, 318: aminodiol derivative HIV-1 protease inhibitor (Bristol-Myers-Squibb); d4API: 9-[2,5-dihydro-5-(phosphonomethoxy)-2-fuiranyl]adenine (Gilead); stavudine: d4T, 2',3'-didehydro-3'-deoxythymidine (Bristol-Myers-Squibb); HBY097: S-4-isopropoxycarbonyl-6-methoxy-3-(methylthio-methyl)-3,4-dihydroquinoxalin-2 (1H)-thione; HEPT: 1-[(2-hydroxyethoxy)methyl]6-(phenylthio)thymine; KNI-272: (2S,3S)-3-amino-2-hydroxy-4-phenylbutyric acid-containing tripeptide; L-697, 593; 5-ethyl-6-methyl-3-(2-phthalimido-ethyl)pyridin-2 (1H)-one; L-735,524: hydroxy-aminopentane amide HIV-1 protease inhibitor (Merck); L-697,661: 3-{[(-4,7-dichloro-1,3-benzoxazol-2-yl)methyl]amino} -5-ethyl-6-methylpyridin-2(1 H)-one; L-FDDC: (−)-β-L-5-fluoro-2',3'-dideoxycytidine; L-FDOC: (−)-β-L-5-fluoro-dioxolane cytosine; nevirapine: 11-cyclopropyl-5,11-dihydro-4-methyl-6H-dipyridol [3,2-b:2',3'-e]diazepin-6-one (Boehringer-Ingelheim); PFA: phosphonofonnate (foscarnet; Astra); PMEA: 9-(2-phosphonylmethoxyethyl) adenine (Gilead); PMPA: (R)-9-(2-phosphonylmethoxypropyl)adenine (Gilead); Ro 31-8959: hydroxyethylamine derivative HIV-1 protease inhibitor (Roche); RPI-3121: peptidyl protease inhibitor, 1-[(3s)-3-(n-alpha-benzyloxycarbonyl)-1-asparginyl)-amino-2-hydroxy-4-phenylbutyryl] -n-tert-butyl-1-proline amide; 2720: 6-chloro-3,3-dimethyl-4-(isopropenyloxycarbonyl)-3, 4-dihydro-quinoxalin-2(1H)thione; SC-52151: hydroxyethylurea isostere protease inhibitor (Searle); SC-55389A: hydroxyethyl-urea isostere protease inhibitor (Searle); TIBO R82150: (+)-(5S)-4,5,6,7-tetrahydro-5-methyl-6-(3-methyl-2-butenyl)imidazo[4,5,1-jk] [1,4]-benzodiazepin-2(1H)-thione (Janssen); TIBO 82913: (+)-(5S)-4,5,6,7,-tetrahydro-9-chloro-5-methyl-6-(3-methyl-2-butenyl)imidazo[4,5,1jk]-[1,4]benzodiazepin-2(1 H)-thione (Janssen); TSAO-m3T: [2',5'-bis-O-(tert-butyldimethylsilyl)-3'-spiro-5'-(4'-amino-1,2'-oxathiole-2',2'-dioxide)]-β-D-pentofuranosyl-N3-methylthymine; U90152:1-[3-[(1-methylethyl)-amino]2-pyridinyl]-4-[[5-[(methylsulphonyl)-amino]-1H-indol-2yl] carbonyl]piperazine; UC: thiocarboxanilide derivatives (Uniroyal); UC-781=N-[4-chloro-3-(3-methyl-2-butenyloxy)phenyl]-2-methyl-3-furancarbothioamide; UC-82=N-[4-chloro-3-(3-methyl-2-butenyloxy)phenyl]-2-methyl-3-thiophenecarbothioamide; VB 11,328: hydroxyethylsulphonamide protease inhibitor (Vertex); VX-478: amprenavir, 141W94, hydroxyethylsulphonamide protease inhibitor (Vertex/Glaxo Wellcome); XM 323: cyclic urea protease inhibitor (Dupont Merck), famciclovir, gancyclovir, and penciclovir. In another embodiment, CS-87 is administered in combination with a protease inhibitor (LG 1350) of the structure:

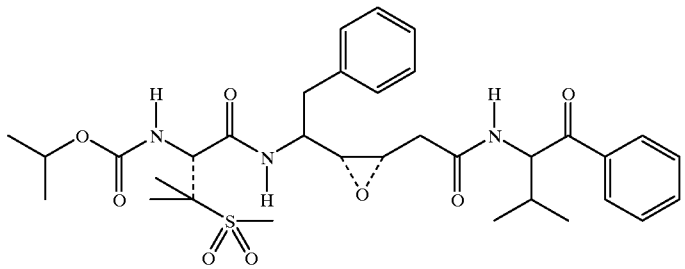

EXAMPLE 1
Development of Mutations in HIV-1 Infected Human Peripheral Blood Mononuclear Cells Under Different Experimental Conditions An HIV-1 line probe assay (LiPA) and sequencing analysis was used to monitor and detect the kinetics of drug-resistant mutations as they develop in culture. The compounds evaluated include the nucleosides CS-87 (CS-87, 3'-azido-2',3'-dideoxyuridine); (−) FTC [(−)-β-2',3'-dideoxy-3'-thia-5-fluorocytidine], 3TC, [(−)-β-2',3'-dideoxy-3'-thiacytidine], CS-92 (AZMC, 3'-azido-2',3'-deoxy-5-methylcytidine), β-D- and β-L-D4FC, (β-L-2',3'-didehydro-2',3'-dideoxy-5-fluorocytidine), a new β-L-purine nucleoside (L-DDA-prodrug), β-L-5-fluoro-2',3'-dideoxycytidine (L-FddC), and the protease inhibitors nelfinavir and amprenavir (VX-478). The results are provided in Table 4 and FIGS. 1–9.

HIV-1 was exposed to increasing drug concentrations while being passed for several weeks in human peripheral blood mononuclear (PBM) cells. Virus from the culture supernatant was amplified by PCR and analyzed by both HIV-1 RT and protease LiPA. Selected samples were also sequenced. The genotypic data was analyzed to reveal the patterns of developing mutations in the cultured drug resistant viruses. The resulting data indicate that real-time analysis of resistance development in culture is possible using this system.

Methodology

Cells and viruses. The methodologies for evaluating the compounds against HIV-1 have been reported previously (Schinazi R F, Lloyd R M, Jr., Nguyen M -H, Cannon D L, McMillan A, Ilksoy N, Chu C K, Liotta D C, Bazmi H Z, Mellors J W. Characterization of human immunodeficiency viruses resistant to oxathiolane-cytosine nucleosides. Antimicrob Agents Chemother 1993;37(4):875–881; Schinazi RF, McMillan A, Cannon D, Mathis R, Lloyd R M, Peck A, Sommadossi J -P, St. Clair M, Wilson J, Furman P A, Painter G, Choi W -B, Liotta D C. Selective inhibition of human immunodeficiency viruses by racemates and enantiomers of cis-5-fluoro-1-[2-(hydroxymethyl)-1,3-oxathiolan-5-yl] cytosine. Antimicrobial Agents Chemother 1992;36(11) :2423–243 1.

Human PBM cells from healthy donors, seronegative for HIV-1 and hepatitis B virus, were isolated by a single-step Ficoll-Hypaque discontinuous gradient centrifugation (Sigma, St. Louis, Mo.) and propagated as described previously (Schinazi R F, Sommadossi J P, Saalmann V, Cannon D L, Xie M -Y, Hart G C, Smith G A, Hahn E F. Activity of 3'-azido-3'-deoxythymidine nucleotide dimers in primary lymphocytes infected with human immunodeficiency virus type 1. Antimicrob Agents Chemother 1990;34:1061–1067.) The prototype strain of HIV-1/LAI obtained from the Centers for Disease Control and Prevention, Atlanta, Ga., was used as the standard virus for the studies in human PBM cells.

Selection of drug-resistant viruses. Bulk HIV-1 infected 3-day-old phytohemagglutinin (PHA) stimulated human PBM cells ($10^6$ cells/ml) were placed in a 25 cm2 flask, and exposed to the compound at a concentration approximately equal to 1 to 10-fold the median effective antiviral concentration ($EC_{50}$) for each drug against low passage parental virus. Untreated infected and uninfected cells served as controls for each passage. The cells were incubated with compounds prior to virus inoculation at a multiplicity of infection of 0.01 for one hour before addition of the virus. After one week of incubation in 5% $CO_2$-air at 37° C., all the cells and media were removed from the flask and centrifuged at 700 g for 10 min. The supernatant (15 ml) was saved for RT activity determination and for preparation of a virus stock for drug-susceptibility assays. The RT activity of the supernatant obtained from virus infected drug-treated cells was compared to that from supernatant obtained from infected untreated cells at different weekly cycles, as described previously. Half the cells and media were placed in a new flask containing uninfected mitogen-stimulated PBM cells, and fresh drug at the desired concentration was added. Drug concentration was increased when 75% inhibition of virus growth was observed on day six. This procedure was repeated each week for several weeks. Virus stock from each weekly cycle was prepared by cell-free virus infection of human PBM cells.

Cell pellets were washed, centrifuiged, lysed and the proviral DNA extracted as previously described. Cytotoxicity of the compounds was determined using the Promega Cell Titer 96 dye uptake assay (Madison, Wis.) in 1–2 day PHA-stimulated PBM cells after 5 days in culture. The median effective concentration ($EC_{50}$) and inhibitory concentration ($IC_{50}$) were derived from the computer-generated median effect plot of the dose-effect data, as described previously.

Sequencing. Each sample PCR product was gel purified by electroelution into Spectra/Por membrane (MW cutoff 12–14,000). Approximately 150 ng of purified PCR product was sequenced using an Autocycle sequencing kit from Pharmacia Biotech (Piscataway, N.J.). Cycle sequencing reactions are conducted according to the manufacturer's recommendations. Briefly, each sample is subjected to 35 cycles of PCR with a denaturation of 95° C. for 1 minute, annealing at 47° C. for 1 minute, and elongation at 70° C. for 1.5 min. After PCR, each reaction is terminated using a stop/loading dye provided in the kit. Samples are then heated to 80° C. for 3 min to denature and then loaded onto a Pharmacia ALF sequencer. Data were analyzed using the ALF Manager software version 2.6.

Line Probe Assay (LiPA). Rapid detection of mutations in the RT region of the HIV genome was determined by LiPA, using INNO-LiPA kits (Innogenetics, Gent, England). A detailed description of this methodology was recently described by Stuyver L., et al. (Stuyver L, Wyseur A, Rombout A, Louwagie J, Scarcez T, Verhofstede C, Rimland D, Schinazi RF, Rossau R. Line probe assay for rapid detection of drug-selected mutations in the human immunodeficiency virus type 1 reverse transcriptase gene. Antimicrob Agents Chemother 1997;41(2):284–91). The protease LiPA is still under development at Innogenetics, Belgium.

As seen, rapid genotyping analysis revealed the different kinetics and mutations obtained by in vitro selection in primary human cells exposed to nucleosides and protease inhibitors. The ability to sample these cultures and detect early mixed mutations through LiPA analysis provided a useful means of establishing appropriate drug pressure in vitro. The in vitro system provides a means to detect a link between protease and RT mutations under VX-478 selection.

Of significance was the finding that the L-nucleosides 3TC, (−) and racemic FTC, β-L-FddC, β-L-D4FC and the β-L-purine nucleoside all selected for the V 184 mutation in HIV-1 infected PBM cells, even though the first four are pyrimidine nucleosides and the fifth is a purine nucleoside.

β-L-D4FC also selected for K/R65 in addition to VI 84, indicating that these two mutations are linked and compatible in vitro.

As indicated in FIG. 1, CS-87 induced a transient mutation at the 70th codon in the reverse transcriptase region.

EXAMPLE 2

Development of Mutations in HIV-1 Infected Human PBMC Under Different Experimental Conditions Table 4 sets out the development of mutations in HIV-1 infected human PBMC under different experimental conditions. Table 5 describes the effect of CS-87 on mutant strains of viruses in human PBM cells.

As shown, viruses which exhibit site directed mutations at other than the 70 codon in the RT region remain sensitive to CS-87. AZT-exposed virus exhibit a deceased sensitivity to CS-87, likely because AZT-exposed virus can exhibit a 70 codon mutation over time.

The mutant viruses tested are as follows: xxBRU Pitt (wild type HIV-1; the backbone used to prepare the other site directed mutagens); MI 84V (methionine to valine change at codon 184); K65R (lysine to arginine change at codon 65); T215Y (threonine to tyrosine change at codon 215); MI 84V/T215Y (virus with both mutations); 215/41 (virus with two mutations (threonine to tyrosine change at codon 215)

and M41L (methionine to leucine change at codon 41)); 4X AZT (virus with four mutations associated with AZT therapy); D67N (aspartic acid to asparagine change at codon 67); K70R lysine to arginine change at codon 70); T215Y (defined as above); K219Q (lysine to glutamine change at codon 219); 964 pre (virus from a patient before he was on AZT therapy, and thus AZT sensitive); and 964 post (virus taken from the same patient after he was on AZT therapy, and thus is AZT resistant).

TABLE 4

Development of Mutations in HIV-1 Infected Human PBMC Under Experimental Conditions

| Compound | Mixed Mutation | Week[a] | Full Mutation | Week[a] |
| --- | --- | --- | --- | --- |
| (−)-BCH-189 | M/V184 | 2 | V184 | 4 |
| (−)-FTC | V/M184 | 2 | V184 | 3 |
| L-FddC | V/M184 | 5 | V184 | 8 |
| Nelfinavir | D/M30 | 5 | — | — |
|  | M/I46 | 5 | — | — |
| CS-092 | K/R70 | 6 | R70 | 18 |
| L-DDA-Prodrug | M/V184 | 6 | — | — |
| L-D4FC[c] | M/V184 | 7 | V184 | 11 |
|  | K/R65 | 15 | R65 | 17 |
| CS-087 | K/R70 | 8 | —[b] | — |
| VX-478 | I/V50 | 8 | V50 | 10 |

[a]Week when first observed on passage in human PBM cells
[b]Transient Mutation. Not found at week 21 or later
[c]Virus cultured in CEM cells

TABLE 5

| Virus | CS-087 $EC^{50}$ μM | $EC^{90}$ μM | Slope | $FI^{50}$ | $GFI^{90}$ |
| --- | --- | --- | --- | --- | --- |
| HIV-1/LAI* | 0.2 | 4.7 | 0.70 | — | — |
| CS-092 res. virus | — | — | — | — | — |
| xxBRU Pitt. | 1.1 | 7.3 | 1.16 | — | — |
| M184V Pitt. | 0.6 | 2.4 | 1.55 | 0.6 | 0.3 |
| K65R Pitt. | 1.1 | 12 | 0.92 ± 0.07 | 1.0 | 1.6 |
| T215Y Pitt. | 0.3 | 2.7 | 1.00 ± 0.11 | 0.3 | 0.4 |
| M184V/T215Y Pitt. | 1.1 | 5.9 | 1.40 | 1.0 | 0.8 |
| 215/4I Pitt. | 2.1 | 19.1 | 0.95 | 1.9 | 2.6 |
| 4X AZT Pitt. | 0.3 | 17.0 | 0.54 | 0.3 | 2.3 |
| L74V Pitt. | 0.6 | 3.8 | 1.18 ± 0.10 | 1.5 | 0.5 |
| AZT-Sen. (964 pre) | 0.4 | 11.1 | 0.65 ± 0.08 | — | — |
| AZT-Post (964 post) | 16.5 | 63 | 1.64 | 87 | 14 |

Averages for data are italicized in the above table.
* = HIV1/LAI average data is taken from drugs tested against mycoplasma free Post 64.
FI (Fold Increase) $EC^{50}$ = $EC^{50}$ data from resistant virus/$EC^{50}$ data from xxBRU Pitt.
FI (Fold Increase) $EC^{90}$ = $EC^{90}$ data from resistant virus/$EC^{90}$ data from xxBRU Pitt.

IV. Treatment of Multiple-Drug Resistant Forms of HIV

The phenotypic resistance profile of the experimental compound (CS-87) (Novirio Pharmaceuticals, Ltd.) and a number of HIV-1 Non-Nucleoside Reverse Transcriptase Inhibitors (NNRTIs), Nucleoside Reverse Transcriptase Inhibitors (NRTIs) and Protease Inhibitors (Pis) were determined using the Antivirogram® recombinant virus approach (Virco). The aim of the study was to determine the potency of the inhibitory effect of a new generation of NRTIs on Multi Drug Resistant isolates and to compare it with their effect on wild-type HIV-1 isolates. All recombinant viruses were taken from the VIRCO repository of phenotypically and genotypically characterized virus isolates. Hirsch et al. Antiretroviral Drug Resistance Testing in Adults with HIV Infection. JAMA; 1998: 79(24) 1984–1991. See also Pauwels et al. Comprehensive HIV drug Resistance monitoring using rapid, high-throughput phenotypic and genotypic assays with correlative data analysis. Antiviral Therapy, 1998: 3: 35 Abstract 51.

All recombinant viruses were taken from the VIRCO repository of phenotypically and genotypically characterized virus isolates.

Phenotypic drug susceptibility determination of recombinant virus isolates is described in Hertogs et al. A Rapid Method for Simultaneous Detection of Phentypic Resistance to Inhibitors of Protease and Reverse Transcriptase in Recombinant HIV-1 Isolates from Patients Treated with Antiretroviral Drugs. Antimicrob. Agents Chemother. 1998; 42(2): 269–276. The basic principle of the Antivirogramg) technology is the construction of chimeric HIV-1 strains composed of the protease (PR) and reverse transcriptase (RT) gene sequences which are isolated and amplified from patient viral RNA. Amplicons are subsequently transfected into CD4+T cells together with a standard laboratory isogenic (HXB2) HIV-1 DNA construct from which the PR/RT gene sequences were deleted. After homologous recombination, new viruses whose diversity reflects the original population amplified from the plasma are produced at high level from these cells.

The virus infectivity ($CCID_5$o) is determined by an endpoint dilution method. The titer is calculated from the degree of infection, measured by the intensity of reporter-gene signal as generated by serial dilutions of the virus shock. The chimeric (clinical isolates and wild-type reference) viruses are then analyzed for their phenotypic sensitivity (i.e. susceptibility) to the different PR and RT-inhibitors in an automated reporter gene-based assay using serial dilutions of the compound. The standardisation of the AntivirogramID assay allows for simultaneous testing of all clinically approved drugs in one 384-well microtiter plate. The experimental drugs are included in separate plates. Each plate contains multiple replicates of mock-infected wells, virus-infection control wells and blank (medium-only) well. All plates are tested in duplicate. 50% Inhibitory concentrations are calculated based on reporter signals obtained through optical reading of 384-well plates containing serial dilutions of compounds, a normalised quantity of virus and by taking into account all relevant control wells. Approval (or not) is done according to critical ranges and settings as described in the corresponding VIRCO Standard Operating Procedure.

A more detailed description of the protocol is as follows. Samples were stored frozen.

The technique included the following steps: total RNA extraction, PR/RT-medated cDNA synthesis using HIV-1 specific primers, amplification of HIV-1 DNA by two consecutive (nested) PCR steps, gel analysis of PCR products, electroporation of PCR products and HIV-1 proviral DNA with PR-RT deletion in MT-4 cells, reculturing of stored chimeric viruses in electroporated cultures, infetivity titer determination by limiting end-point dilution method, preparation of test plates (in duplicates, 4 wells per test concentration) with serial dilutions of test compounds, and then addition of titrated virus and MT 4 virus. To confirm the genotypic pattern, genotyping (ABI-sequencing) was performed after recombination and culture of the laboratory strains by analysis of cell viability, calculation of results (dose-response curves, $IC_{50}$ values), and reporting of data.

Antiviral Activity Against Drug-Resistant HIV

Drug-resistant HIV strains have been detected in patients on all of the currently available antiretroviral drug regimens. Incomplete virus suppression together with an error-prone reverse transcriptase and potential viral recombination lead to each patient having numerous quasispecies and promote the emergence of drug-resistant strains. High-level drug resistance can emerge after only several weeks of lamivudine (3TC) and nevirapine therapy where drug-resistant quasispecies likely pre-exist in essentially all patients. Resistance has emerged more slowly for zidovudine (ZDV) which requires the sequential accumulation of multiple mutations to develop high-level resistance. Certain drugs, such as didanosine (ddI), dideoxycytidine (ddC) and stavudine (d4T) have selected viruses with only low-level resistance, despite prolonged therapy.

The first data suggesting a correlation between the emergence of viral resistance and clinical progression was reported by Larder and colleagues in 1989 (Larder, B. A., Darby, G. & Richman, D. D. (1989) *Science* 243, 1731–1734, Larder, B. A. & Kemp, S. D. (1989) *Science* 246, 1155–1158).

Viral isolates from patients failing treatment were isolated and the reverse transcriptase gene sequenced to reveal five distinct mutations conferring viral resistance to ZDV at codons 41, 67, 70, 215, and 219 (20, 26, 27). High-level drug resistance was attributed to the widespread use of ZDV monotherapy which lead to the accumulation of multiple mutations in the reverse transcriptase.

Today's highly active antiretroviral therapy, combines ZDV with other nucleoside or non-nucleoside RT inhibitors and a protease inhibitor but does not include ZDV monotherapy. Although ZDV resistance continues to increase due to mutations at 41, 67, 70, 215 and 219, the accumulation of more than three of these changes in a particular virus isolate has a prevalence of less than 2% in most patient groups (Table 6).

TABLE 6

Prevalence of Zidovudine Resistance Mutations in Various Patient Populations

| Mutation | Kuritzkes (n = 35) % | Perrin/Yerly (n = 61) % | VIRCO (n = 6603) % | Stanford (n = 1100) % |
|---|---|---|---|---|
| 215Y | 0 | 3.3 | 1.5 | 2.1 |
| 215Y, 184V | 8.6 | 3.3 | 1.9 | 0 |
| 41L, 215Y | 2.9 | — | 2.4 | 3.2 |
| 41L, 215Y, 184V | 17 | 3.3 | 7.5 | 0.7 |
| 41L, 67N, 210W, 215Y | 0 | 3.3 | 6.4 | 2.2 |
| 41L, 67N, 210W, 215Y, 184V | 2.9 | 15 | 4.3 | 0.5 |
| 67N, 70R, 215Y, 219Q | 2.9 | — | 1.3 | 1.8 |
| 67N, 70R, 215Y, 219Q, 184V | 0 | — | 0.5 | 0 |
| 41L, 67N, 210W, 215Y, 219Q | 0 | 0 | 1.0 | 0.3 |
| 41L, 67N, 210W, 215Y, 219Q, 184V | 0 | 1.6 | 0.1 | 0.3 |
| 41L, 67N, 70R, 210W, 215Y, 219Q | 0 | 3.3 | 0.8 | 0.3 |
| 41L, 67N, 70R, 210W, 215Y, 219Q, 184V | 0 | 3.3 | 0.1 | 0.1 |

(—): not determined
Kuritzkes: therapeutic failures, Denver (Young, B., Johnson, S., Bahktiarai, M., Shugarts, D., Young, R. K., Allen, M., Ramey II, R. R. & Kuritzkes, D. R. (1998) Journal of Infectious Diseases 178, 1497–1501; Perrin/Yerly: failures, Swiss Cohort (Lorenzi, P., Opravil, M., Hershel, B., Chave, J.-P., Furrer, H.-J., Sax, H., Perneger, T. V., Perrin, L., Kaiser, L., Yerly, S. & and the Swiss HIV Cohort Study (1999) AIDS 13, F17–21; VIRCO: proprietary database, Stanford HIV database: all entries (Shafer, R. W., Stevenson, D. & Chan, B. (1999) Nucleic Acids Research 27, 348–52.

It is now more routine to identify ZDV-resistant strains with fewer ZDV-specific mutations which contain instead mutations associated with both ZDV and 3TC, or NNRTI and protease inhibitor resistance. In addition, the prevalence of the so-called multiple dideoxynucleotide resistant strains (MDR or 151 and 68 or 69 insertion mutants (Winters, M. A., Coolley, K. L., Girard, Y. A., Levee, D. J., Hamdan, H., Shafer, R. W., Katzenstein, D. A. & Merigan, T. C. (1998) *Journal of Clinical Investigation* 102, 1769–75)) and transmission of drug resistant strains remains rare at the present time. One explanation is that the fitness of the mutant reverse transcriptase is diminished reducing the ability of these resistant viruses to propagate.

HIV strains which were found to be resistant in vitro to both ZDV and 3'-azido-2',3'-dideoxyuridine generally contain the five major mutations in the reverse transcriptase gene (41L/D67N/K70R/T215Y/K219Q). Molecular clones or primary clinical isolates of HIV containing less than five of these ZDV-resistance-associated mutations and/or one or two mutations associated with other antiretroviral drugs (e.g., M184V, K103N, Y181C) remain sensitive to 3'-azido-2',3'-dideoxyuridine (<3-fold change in $EC_{50}$) (Table 7).

TABLE 7

Antiviral Activity Against Drug-Resistant HIV

| Virus | Cell Type | 3'Azido-2',3'-dideoxyuridine | | | ZDV | | |
|---|---|---|---|---|---|---|---|
| | | Untreated $EC_{50}$ ($\mu$M) | Selected Variant $EC_{50}$ ($\mu$M) | Fold-resistance | Untreated $EC_{50}$ ($\mu$M) | Selected Variant $EC_{50}$ ($\mu$M) | Fold-resistance |
| Molecular Clones | | | | | | | |
| HIV-1 (T215Y) | PBMC | 1.1[a] | 0.3 | 0.3 | 0.004 | 0.01 | 2.5 |
| HIV-1 (M184V) | PBMC | 1.1[a] | 0.6 | 0.5 | 0.004 | 0.003 | 0.8 |
| HIV-1 (M184V) | MT-2 | 20[a] | 16.8 | 0.8 | 0.006 | 0.009 | 1.5 |
| HIV-1 (K65R) | PBMC | 1.1[a] | 1.1 | 1 | 0.004 | 0.008 | 2 |
| HIV-1 (L74V) | PBMC | 1.1[a] | 0.6 | 0.5 | 0.004 | 0.003 | 0.6 |
| (M184V/T215Y) | PBMC | 1.1[a] | 1.1 | 1 | 0.004 | 0.023 | 5.8 |
| 1 (T215Y/M41L) | PBMC | 1.1[a] | 2.1 | 1.9 | 0.004 | 0.042 | 11 |
| HIV-1 (D67N/K70R/T215Y/K219Q) | PBMC | 1.1[a] | 0.3 | 0.3 | 0.004 | 0.036 | 9 |
| HIV-1 (D67N/K70R/T215Y/K219Q) | MT-2 | 20[a] | >90 | >4.5 | 0.006 | 0.2 | 33 |
| HIV-1 (D67N/K70R/M184V/T215Y/K219Q) | MT-2 | 20[a] | 53.4 | 2.7 | 0.006 | 0.03 | 5 |
| HIV-1 (M41L/D67N/M184V/H208Y/L210W/ | MT-2 | 20[a] | 50.2 | 2.5 | 0.006 | >3.3 | >550 |

TABLE 7-continued

Antiviral Activity Against Drug-Resistant HIV

| Virus | Cell Type | 3'Azido-2',3'-dideoxyuridine | | | ZDV | | |
|---|---|---|---|---|---|---|---|
| | | Untreated $EC_{50}$ (μM) | Selected Variant $EC_{50}$ (μM) | Fold-resistance | Untreated $EC_{50}$ (μM) | Selected Variant $EC_{50}$ (μM) | Fold-resistance |
| R211K/L214F/T215Y) Clinical Isolates (long-term ZDV monotherapy) | | | | | | | |
| HIV-1 (A-161) | MT-4 | 0.6[c] | 8.6 | 14 | 0.02 | 1.2 | 60 |
| HIV-1 (C-246) | MT-4 | 0.6[c] | 10.3 | 17 | 0.02 | 0.7 | 35 |
| HIV-1 (G-68) | MT-4 | 0.6[c] | 0.5 | 0.8 | 0.02 | 0.65 | 33 |
| HIV-1 (R-102) | MT-4 | 0.6[c] | 0.3 | 0.5 | 0.02 | 1.2 | 60 |
| HIV-1 (X-78) | MT-4 | 0.6[c] | 0.5 | 0.8 | 0.02 | 1.1 | 55 |
| HIV-1 (A012D:M41L?/D67N/K70R/T215F/K219Q) | HeLa HT4-6C | 0.4[c] | 89 | 223 | 0.01 | 2 | 200 |
| HIV-1 (A012D:M41L?/D67N/K70R/T215F/K219Q) | PBMC | 0.4[c] | 16.6 | 41 | 0.001 | 0.24 | 240 |
| HIV-1 (A018C:D67N/K70R/T215Y/K219Q) | HeLa HT4-6C | 1[c] | 50 | 50 | 0.01 | 4 | 400 |
| HIV-1 (A036DD:M41L/D67N/K70R/T215Y) | HeLa HT4-6C | 0.6[c] | 56 | 93 | 0.007 | 5.5 | 800 |
| HIV-1 (P022C:M41L?/D67N/K70R/T215F/K219Q) | HeLa HT4-6C | 0.4[c] | 40 | 100 | 0.03 | 5.6 | 187 |
| HIV-1 (P-26B:M41L?/D67N/K70R/T215Y) | HeLa HT5-6C | 0.4[c] | 100 | 250 | 0.01 | 2.8 | 280 |

[a]$EC^{50}$ of parent strain HIV-1 (xxLAI)
[b]$EC^{50}$ of representative ZDV-sensitive isolate
[c]$EC^{50}$ of clinical isolate (pre) from each individual prior to long-term ZDV monotherapy.

Following a detailed review of the available antiviral data a comprehensive analysis of the in vitro activity of 3'-azido-2',3'-dideoxyuridine against drug-resistant HIV was performed using a standarized phenotypic susceptibility assay configured by VIRCO Central Virological Laboratory Limited (Dublin, Ireland) (Hirsch, M. S., Conway, B., D'Aquila, R. T., Johnson, V. A., Brun-Vezinet, F., Clotet, B., Demeter, L. M., Hammer, S. M., Jacobsen, D. M., Kuritzkes, D. R., Loveday, C., Mellors, J. W., Vella, S. & Richman, D. D. (1998) *Journal of the American Medical Association* 279, 1984–91; Hertogs, K., de Bethune, M. P., Miller, V., Ivens, T., Schel, P., Van Cauwenberge, A., Van Den Eynde, C., Van Gerwen, V., Azijn, H., Van Houtte, M., Peeters, F., Staszewski, S., Conant, M., Bloor, S., Kemp, S., Larder, B. & Pauwels, R. (1998) *Antimicrobial Agents and Chemotherapy* 42, 269–76; Pauwels, R. & et al. (1998) *Antiviral Therapy* 3, 35, Abstract 51.

Nineteen different primary clinical isolates, representing the major NRTI (ZDV, ddI, ddC, d4T, 3TC), NNRTI (Nevirapine, Delavirdine, Efavirenz) and protease (Indinavir, Ritonavir, Saquinavir, Nelfinavir) resistant phenotypes were included in the analysis (Table 8). The results of this analysis were similar to that contained in Table 7. In addition, viruses containing the multiple dideoxynucleoside resistance mutations which lead to resistance to all known nucleoside analogs (position 69 insertion(s), Q 151 M substitution (combined with typical ZDV-associated mutations)) were, as expected, also resistant to 3'-azido-2',3'-dideoxyuridine.

TABLE 8

Overall Summary of Phenotypic Resistance of Recombinant Virus Isolates (including RT genotype)

| Genotypic Profile | Compound (fold Resistance) | | |
|---|---|---|---|
| | AZT | 3TC | NV-01 |
| K70R | 0.7 | 1 | 0.2 |
| K70R, K219Q | 5 | 1 | 2 |

TABLE 8-continued

Overall Summary of Phenotypic Resistance of Recombinant Virus Isolates (including RT genotype)

| Genotypic Profile | Compound (fold Resistance) | | |
|---|---|---|---|
| | AZT | 3TC | NV-01 |
| D67N, K70R, K219Q/K, 181C/Y | 12 | 3.7 | 3.6 |
| T215Y | 13.5 | 1.5 | 1 |
| M41L, L210W, T215Y | 24 | 0.4 | 2 |
| M41L, L210L, T315Y, Y181C/Y, M184M/V | >36 | 3 | 2.85 |
| M41L, D67N, K70R, K103N, L210W, T215Y, K219N/K | >36 | 8.25 | 0.8 |
| D67D/N, K70R, M184V, G333E | 0.9 | >99 | 0.6 |
| M41L, T215Y, M184V | 5.5 | >99 | 0.75 |
| M41L, T69S-V-T, L210W, T215Y, G333E | >65 | >65 | >65 |
| T69G, Q151M, M184V/M | >65 | >65 | >65 |
| T69S-E, M1841, T215Y | >65 | >65 | >65 |
| T69I, K70R, Q151M, M184V | >65 | >65 | >65 |

V. Preparation of Pharmaceutical Compositions

Humans suffering from effects caused by any of the diseases described herein, and in particular, HIV infection, can be treated by administering to the patient an effective amount of CS-87 in combination or alternation with an anti-HIV agent that induces a mutation at a location other than the 70 codon in the reverse transcriptase region, or with a pharmaceutically acceptable salt or prodrug thereof in the presence of a pharmaceutically acceptable carrier or diluent. In one embodiment, humans infected with multiple drug resistant forms of HIV can be effectively treated by administering to the patient an effective amount of CS-87 or a pharmaceutically acceptable salt or prodrug thereof in the presence of a pharmaceutically acceptable carrier or diluent. For multiple drug resistant patients, CS-87 is either administered alone or in combination. The active materials can be administered by any appropriate route, for example, orally, parenterally, enterally, intravenously, intradermally, subcutaneously, transdermally, intranasally or topically, in liquid or solid form.

The active compound(s) are included in the pharmaceutically acceptable carrier or diluent in an amount sufficient to deliver to a patient a therapeutically effective amount of compound to inhibit viral replication in vivo, especially HIV replication, without causing serious toxic effects in the treated patient. By "inhibitory amount" is meant an amount of active ingredient sufficient to exert an inhibitory effect as measured by, for example, an assay such as the ones described herein.

A preferred dose of the compound for all the above-mentioned conditions will be in the range from about 1 to 75 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside to be delivered. If the derivative exhibits activity in itself, the effective dosage can be estimated as above using the weight of the derivative, or by other means known to those skilled in the art.

The compounds are conveniently administered in unit any suitable dosage form, including but not limited to one containing 7 to 3000 mg, preferably 70 to 1400 mg of active ingredient per unit dosage form. An oral dosage of 50 to 1000 mg is usually convenient.

Ideally, the active ingredient should be administered to achieve peak plasma concentrations of the active compound of from about 0.02 to 70 micromolar, preferably about 0.5 to 10 $\mu$M. This may be achieved, for example, by the intravenous injection of a 0.1 to 25% solution of the active ingredient, optionally in saline, or administered as a bolus of the active ingredient.

The concentration of active compound in the drug composition will depend on absorption, distribution, metabolism and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible bind agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compounds can be administered as a component of an elixir, suspension, syrup, wafer, chewing gum or the like. A syrup may contain, in addition to the active compounds, sucrose as a sweetening agent and certain preservatives, dyes and colorings and flavors.

The compounds or their pharmaceutically acceptable derivative or salts thereof can also be mixed with other active materials that do not impair the desired action, or with materials that supplement the desired action, such as antibiotics, antifungals, antiinflammatories, protease inhibitors, or other nucleoside or non-nucleoside antiviral agents, as discussed in more detail above. Solutions or suspensions used for parental, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

Liposomal suspensions (including liposomes targeted to infected cells with monoclonal antibodies to viral antigens) are also preferred as pharmaceutically acceptable carriers. these may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

Controlled Release Formulations

All of the U.S. patents cited in this section on controlled release formulations are incorporated by reference in their entirety.

The field of biodegradable polymers has developed rapidly since the synthesis and biodegradability of polylactic acid was reported by Kulkarni et al., in 1966 ("Polylactic acid for surgical implants," *Arch. Surg.*, 93:839). Examples of other polymers which have been reported as useful as a matrix material for delivery devices include polyanhydrides, polyesters such as polyglycolides and polylactide-co-glycolides, polyamino acids such as polylysine, polymers and copolymers of polyethylene oxide, acrylic terminated polyethylene oxide, polyamides, polyurethanes, polyorthoesters, polyacrylonitriles, and polyphosphazenes. See, for example, U.S. Pat. Nos. 4,891,225 and 4,906,474 to Langer (polyanhydrides), U.S. Pat. No. 4,767,628 to Hutchinson (polylactide, polylactide-co-glycolide acid), and U.S. Pat. No. 4,530,840 to Tice, et al. (polylactide, polyglycolide, and copolymers). See also U.S. Pat. No. 5,626,863 to Hubbell, et al which describes photopolymerizable biodegradable hydrogels as tissue contacting materials and controlled release carriers (hydrogels of polymerized and crosslinked macromers comprising hydrophilic oligomers having biodegradable monomeric or oligomeric extensions, which are end capped monomers or oligomers capable of polymerization and crosslinking); and PCT WHO 97/05185 filed by Focal, Inc. directed to multiblock biodegradable hydrogels for use as controlled release agents for drug delivery and tissue treatment agents.

Degradable materials of biological origin are well known, for example, crosslinked gelatin. Hyaluronic acid has been crosslinked and used as a degradable swelling polymer for biomedical applications (U.S. Pat. No. 4,957,744 to Della Valle et. al.; (1991) "Surface modification of polymeric biomaterials for reduced thrombogenicity," Polym. Mater. Sci. Eng., 62:731–735]).

Many dispersion systems are currently in use as, or being explored for use as, carriers of substances, particularly biologically active compounds. Dispersion systems used for pharmaceutical and cosmetic formulations can be categorized as either suspensions or emulsions. Suspensions are defined as solid particles ranging in size from a few manometers up to hundreds of microns, dispersed in a liquid medium using suspending agents. Solid particles include microspheres, microcapsules, and nanospheres. Emulsions are defined as dispersions of one liquid in another, stabilized by an interfacial film of emulsifiers such as surfactants and lipids. Emulsion formulations include water in oil and oil in water emulsions, multiple emulsions, microemulsions, microdroplets, and liposomes. Microdroplets are unilamellar phospholipid vesicles that consist of a spherical lipid layer with an oil phase inside, as defined in U.S. Pat. Nos. 4,622,219 and 4,725,442 issued to Haynes. Liposomes are phospholipid vesicles prepared by mixing water-insoluble polar lipids with an aqueous solution. The unfavorable entropy caused by mixing the insoluble lipid in the water produces a highly ordered assembly of concentric closed membranes of phospholipid with entrapped aqueous solution.

U.S. Pat. No. 4,938,763 to Dunn, et al., discloses a method for forming an implant in situ by dissolving a nonreactive, water insoluble thermoplastic polymer in a biocompatible, water soluble solvent to form a liquid, placing the liquid within the body, and allowing the solvent to dissipate to produce a solid implant. The polymer solution can be placed in the body via syringe. The implant can assume the shape of its surrounding cavity. In an alternative embodiment, the implant is formed from reactive, liquid oligomeric polymers which contain no solvent and which cure in place to form solids, usually with the addition of a curing catalyst.

A number of patents disclose drug delivery systems that can be used to administer CS-87 or a nucleotide or other defined prodrug thereof. U.S. Pat. No. 5,749,847 discloses a method for the delivery of nucleotides into organisms by electroporation. U.S. Pat. No. 5,718,921 discloses microspheres comprising polymer and drug dispersed therewithin. U.S. Pat. No. 5,629,009 discloses a delivery system for the controlled release of bioactive factors. U.S. Pat. No. 5,578,325 discloses nanoparticles and microparticles of non-linear hydrophilic hydrophobic multiblock copolymers. U.S. Pat. No. 5,545,409 discloses a delivery system for the controlled release of bioactive factors. U.S. Pat. No. 5,494,682 discloses ionically cross-linked polymeric microcapsules.

U.S. Pat. No. 5,728,402 to Andrx Pharmaceuticals, Inc. describes a controlled release formulation that includes an internal phase which comprises the active drug, its salt or prodrug, in admixture with a hydrogel forming agent, and an external phase which comprises a coating which resists dissolution in the stomach. U.S. Pat. Nos. 5,736,159 and 5,558,879 to Andrx Pharmaceuticals, Inc. discloses a controlled release formulation for drugs with little water solubility in which a passageway is formed in situ. U.S. Pat. No. 5,567,441 to Andrx Pharmaceuticals, Inc. discloses a once-a-day controlled release formulation. U.S. Pat. No. 5,508,040 discloses a multiparticulate pulsatile drug delivery system. U.S. Pat. No. 5,472,708 discloses a pulsatile particle based drug delivery system. U.S. Pat. No. 5,458,888 describes a controlled release tablet formulation which can be made using a blend having an internal drug containing phase and an external phase which comprises a polyethylene glycol polymer which has a weight average molecular weight of from 3,000 to 10,000. U.S. Pat. No. 5,419,917 discloses methods for the modification of the rate of release of a drug form a hydrogel which is based on the use of an effective amount of a pharmaceutically acceptable ionizable compound that is capable of providing a substantially zero-order release rate of drug from the hydrogel. U.S. Pat. No. 5,458,888 discloses a controlled release tablet formulation.

U.S. Pat. No. 5,641,745 to Elan Corporation, plc discloses a controlled release pharmaceutical formulation which comprises the active drug in a biodegradable polymer to form microspheres or nanospheres. The biodegradable polymer is suitably poly-D,L-lactide or a blend of poly-D,L-lactide and poly-D,L-lactide-co-glycolide. U.S. Pat. No. 5,616,345 to Elan Corporation plc describes a controlled absorption formulation for once a day administration that includes the active compound in association with an organic acid, and a multi-layer membrane surrounding the core and containing a major proportion of a pharmaceutically acceptable film-forming, water insoluble synthetic polymer and a minor proportion of a pharmaceutically acceptable film-forming water soluble synthetic polymer. U.S. Pat. No. 5,641,515 discloses a controlled release formulation based on biodegradable nanoparticles. U.S. Pat. No. 5,637,320 discloses a controlled absorption formulation for once a day administration. U.S. Pat. Nos. 5,580,580 and 5,540,938 are directed to formulations and their use in the treatment of neurological diseases. U.S. Pat. No. 5,533,995 is directed to a passive transdermal device with controlled drug delivery. U.S. Pat. No. 5,505,962 describes a controlled release pharmaceutical formulation.

This invention has been described with reference to its preferred embodiments. Variations and modifications of the invention, will be obvious to those skilled in the art from the foregoing detailed description of the invention. It is intended that all of these variations and modifications be included within the scope of this invention.

We claim:

1. A method for treating a human infected with HIV comprising administering CS-87 (3'-azido-2',3'-dideoxyuridine) or its pharmaceutically acceptable salt or prodrug in alternation or combination with a second anti-HIV drug that induces a mutation in HIV at a location other than the 70th codon of the reverse transcriptase region of HIV.

2. The method of claim 1, wherein the second anti-HIV drug is a protease inhibitor.

3. The method of claim 2, wherein the protease inhibitor is indinavir ({1(1S, 2R) 5(S)}-2,3,5-trideoxy-N-(2,3-dihydro-2-hydroxy-1H-inden-1-yl)-5-{2-{{(1,1-dimethylethyl)amino}carbonyl}-4-(3-pyridinylmethyl)-1-piperazinyl}-2-(phenylmethyl)-D-erythro-pentoamide sulfate), nelfinavir, saquinavir, ritonavir, ABT-378 (N-(4(S)-(2-(2,6-dimethylphenoxy)-acetylamino)-3(S)-hydroxy-5-phenyl-1(S)-benzylpentyl)-3-methyl-2-(S)-(2-oxo(1,3-diazaperhydroxinyl)butanamine)), or amprenavir.

4. The method of claim 1, wherein the second anti-HIV drug is a nucleoside analogue or a nucleotide analogue.

5. The method of claim 4, wherein the nucleoside analogue is FTC (cis-2',3'-dideoxy-3'-thia-5-fluorocytidine), 3TC (β-L-3'-thia-2',3'-dideoxycytidine), DDI (2',3'-dideoxyinosine), dd4FC (2',3'-dideoxy2',3'-didehydro-5-fluorocytidine), DAPD (β-D-dioxolanyl-2,6-diaminopurine), FddA (2',3',-dideoxy-2'-beta-fluoroadenosine), or abacavir ({(1S, 4R)-4-{2-amino-6-(cyclopropyl)amino-9H-purin-9-yl}-2-cyclopentene-1-methanol}.

6. The method of claim 4, wherein the nucleotide analogue is adefovir {bis(pivaloyloxymethyl)-9-(2-phosphonylmethoxyethyl)adenine} or PMPA ((R)-9-(2-phosphonyl-methoxypropyl)adenine).

7. The method of claim 1, wherein the second anti-HIV drug is a non-nucleoside reverse transcriptase inhibitor.

8. The method of claim 7, wherein the non-nucleoside reverse transcriptase inhibitor is efavirenz, nevirapine, MKC-442 {1-ethoxymethyl-5-isopropyl-6-benzyluracil}, AG-1549 (capravirine: 5-(3,5-dichlorophenyl)thio-4-isopropyl-1-(4-pyridyl)methyl-1H-imidazol-2-ylmethyl carbamate), or delavirdine.

9. The method of claim 1, wherein the second anti-HIV drug is an HIV-integrase inhibitor or a chemokine inhibitor or a fusion inhibitor.

10. A method for assessing the sensitivity of HIV-1 to CS-87 in a patient to whom CS-87 has been administered, comprising isolating a sample of HIV-1 from the patient and identifying whether a mutation has occurred at codon 70 in the reverse transcriptase region of the virus.

11. A method for treating a patient infected with a strain of HIV that is resistant to treatment with an anti-HIV agent selected from the group consisting of 3TC (β-L-3'-thia-2',3'-dideoxycytidine), DDI (2',3'-dideoxyinosine), DDC (2',3'-dideoxycytidine), [(–) and racemic] FTC (cis-2',3'-dideoxy-3'-thia-5-fluorocytidine), dd4FC (2',3'-dideoxy-2',3'-didehydro-5-fluorocytidine), DAPD (β-D-dioxolanyl-2,6-diaminopurine), FddA (2',3',-dideoxy-2'-beta-fluoroadenosine), abacavir ((1S,4R)-4-{2-amino-6-(cyclopropylamino)-9H-purin-9-yl}-2-cyclopentene-1-methanol succinate), nevirapine (11-cyclopropyl-5,11-dihydro-4-methyl-6H-dipyrido{3,2-b:2',3'-e}diazepin-6-one), delavirdine (1-(3-(1-methyl-ethyl)amino)-2-pyridinyl-4-((5-((methylsulfonyl)amino)-1H-indol-2-yl)carbonyl)-, monoethanesulfonate), efavirenz (1,4-dihydro-2H-3,1-benzoxazin-2-one), indinavir ({1(1,S,2R),5(S)}-2,3,5-trideoxy-N-(2,3-dihydro-2-hydroxy-1H-inden-1-yl)-5-{2-{{(1,1-dimethylethyl)amino}carbonyl}-4-(3-pyridinylmethyl)-1-piperazinyl}-2-(phenylmethyl)-D-erythro-pentoamide sulfate)), nelfinavir ({3S-{2(2S*,3S*),3-alpha,4-a-beta,8a-beta-}}-N-(1,1-dimethylethyl) decahydro-2-)2-hydroxy-3-{(3-hydroxy-2-methylbenzoyl)amino}-4-(phenylthio)butyl}-3-isoquinolincarboxamide monomethanesulfonate), ritonavir, saquinavir (N-tert-butyl-decahydro-2-{2(R)-hydroxy-4-phenyl-3(S)-{{N-(2-guinolylcarbony l)-L-asparaginyl}amino}butyl}-(4aS,8aS)-isoguinoline-3(S)-carboxamide), amprenavir ((S)-tetrahydrofuran-3-yl-N-{(1S,2R)-3-{N-{(4-aminophenyl) sulfonyl}-N-isobutylamino}-1-benzyl-2-hydroxypropyl}carbamate), MKC-442 (6-benzyl-1-ethoxymethyl-5-isopropyluracil), ABT-378 (N-(4(S)-(2-(2, 6-dimethylphenoxy)-acetylamino)-3(S)-hydroxy-5-phenyl-1(S)-benzylpentyl)-3-methyl-2-(S)-(2-oxo(1,3-diazaperhydroxinyl)butanamine), AG-1549, d4T (2',3'-didehydro-3'-deoxythymidine), and AZT (3'-azido-3'-deoxythymidine), comprising administering an effective amount of CS-87 or its pharmaceutically acceptable prodrug or salt to the patient optionally in a pharmaceutically acceptable carrier.

12. The method of claim 11, wherein the anti-HIV agent is 3TC.

13. The method of claim 11, wherein the anti-HIV agent is DDC.

14. The method of claim 11, wherein the anti-HIV agent is DDI.

15. The method of claim 11, wherein the anti-HIV agent is nevirapine.

16. The method of claim 11, wherein the anti-HIV agent is delavirdine.

17. The method of claim 11, wherein the anti-HIV agent is efavirenz.

18. The method of claim 11, wherein the anti-HIV agent is indinavir.

19. The method of claim 11, wherein the anti-HIV agent is nelfinavir.

20. The method of claim 11, wherein the anti-HIV agent is ritonavir.

21. The method of claim 11, wherein the anti-HIV agent is saquinavir.

22. The method of claim 11, wherein the anti-HIV agent is AZT.

23. The method of claim 11, wherein the anti-HIV agent is D4T.

24. The method of claim 11, wherein the anti-HIV agent is dd4FC.

25. The method of claim 11, wherein the anti-HIV agent is DAPD.

26. The method of claim 11, wherein the anti-HIV agent is FddA.

27. The method of claim 11, wherein the anti-HIV agent is (–) and racemic FTC.

28. The method of claim 11, wherein the anti-HIV agent is abacavir.

29. The method of claim 11, wherein the anti-HIV agent is amprenavir.

30. The method of claim 11, wherein the anti-HIV agent is MKC-442.

31. The method of claim 11, wherein the anti-HIV agent is ABT-749.

32. The method of claim 11, wherein the anti-HIV agent is AG-1549.

* * * * *